(12) United States Patent
Reed et al.

(10) Patent No.: US 9,664,608 B2
(45) Date of Patent: May 30, 2017

(54) CHARACTERIZATION OF POLYMER AND COLLOID SOLUTIONS

(71) Applicant: ADVANCED POLYMER MONITORING TECHNOLOGIES, INC., New Orleans, LA (US)

(72) Inventors: Wayne Frederick Reed, New Orleans, LA (US); Michael Felix Drenski, New Orleans, LA (US); Alex Wayne Reed, New Orleans, LA (US)

(73) Assignees: ADVANCED POLYMER MONITORING TECHNOLOGIES, INC., New Orleans, LA (US); THE ADMINISTRATORS OF THE TULANE EDUCATIONAL FUND, New Orleans, LA (US)

(*) Notice: Subject to any disclaimer, the term of this patent is extended or adjusted under 35 U.S.C. 154(b) by 101 days.

(21) Appl. No.: 14/464,658

(22) Filed: Aug. 20, 2014

(65) Prior Publication Data

US 2015/0056710 A1  Feb. 26, 2015

Related U.S. Application Data

(60) Provisional application No. 61/868,050, filed on Aug. 20, 2013, provisional application No. 62/002,111, filed on May 22, 2014.

(51) Int. Cl.
*G01N 15/02* (2006.01)
*G01N 21/51* (2006.01)
(Continued)

(52) U.S. Cl.
CPC ......... *G01N 15/0211* (2013.01); *G01N 21/51* (2013.01); *G01N 21/53* (2013.01);
(Continued)

(58) Field of Classification Search
CPC .......... G01N 15/0205; G01N 15/0211; G01N 15/1459; G01N 2021/4711;
(Continued)

(56) References Cited

U.S. PATENT DOCUMENTS 3,708,402 A   1/1973   Bean
5,093,030 A   3/1992   Ito et al.
(Continued)

FOREIGN PATENT DOCUMENTS

EP   0582431 A2   2/1994
GB   2369182 A    5/2002
(Continued)

OTHER PUBLICATIONS

Extended European Search Report mailed Mar. 7, 2017 in corresponding EP Application No. 14837165.1, filed Aug. 20, 2014, titled, "Characterization of Polymer and Colloid Solutions" to Applicant Advanced Polymer Monitoring Technologies, Inc., 8 pages.

(Continued)

*Primary Examiner* — Maureen Wallenhorst
(74) *Attorney, Agent, or Firm* — Polsinelli PC

(57) ABSTRACT

Simultaneous Multiple Sample Light Scattering systems and methods can be used for polymer stability testing and for applying stressors to polymer or colloid solutions including heat stress, ultrasound, freeze/thaw cycles, shear stress and exposure to different substances and surfaces, among others, that create a polymer stress response used to characterize the polymer solution and stability.

21 Claims, 16 Drawing Sheets

(51) Int. Cl.
*G01N 21/75* (2006.01)
*G01N 33/68* (2006.01)
*G01N 21/53* (2006.01)
*G01N 21/47* (2006.01)

(52) U.S. Cl.
CPC .. *G01N 33/6803* (2013.01); *G01N 2021/4711* (2013.01); *G01N 2021/4719* (2013.01); *G01N 2021/4726* (2013.01); *G01N 2021/4792* (2013.01); *G01N 2201/0612* (2013.01); *G01N 2201/08* (2013.01); *G01N 2201/1224* (2013.01)

(58) Field of Classification Search
CPC ... G01N 2021/4719; G01N 2021/4726; G01N 2021/4792; G01N 21/51; G01N 21/53; G01N 21/90; G01N 2201/0612; G01N 2201/08; G01N 2201/1224; G01N 33/68; G01N 33/6803
USPC ..... 436/43, 86, 164; 422/68.1, 82.05, 82.09; 356/335, 336, 337, 338, 341, 342, 343, 356/435, 444; 702/22
See application file for complete search history.

(56) References Cited

U.S. PATENT DOCUMENTS

| | | | |
|---|---|---|---|
| 5,739,003 A | 4/1998 | Brocklehurst et al. | |
| 6,144,032 A * | 11/2000 | Gazdzinski | G01N 23/222 250/269.6 |
| 6,238,940 B1 * | 5/2001 | Steffan | H01L 22/20 257/E21.525 |
| 6,618,144 B1 * | 9/2003 | Reed | G01N 15/0211 356/336 |
| 6,751,599 B2 | 6/2004 | Chang et al. | |
| 7,612,325 B1 * | 11/2009 | Watkins, Jr. | G01N 27/12 250/221 |
| 2001/0054356 A1 * | 12/2001 | Newman | A61M 1/0281 96/156 |
| 2009/0046274 A1 | 2/2009 | McHugh et al. | |
| 2009/0306311 A1 | 12/2009 | Reed | |
| 2012/0076860 A1 | 3/2012 | Trout et al. | |
| 2012/0196356 A1 | 8/2012 | Wagner et al. | |
| 2012/0329128 A1 * | 12/2012 | Hasslacher | A61K 47/26 435/188 |

FOREIGN PATENT DOCUMENTS

| | | |
|---|---|---|
| WO | 02/21108 A2 | 3/2002 |
| WO | 2009/149328 A2 | 12/2009 |

OTHER PUBLICATIONS

Michael F. Drenski et al: "Monitoring protein aggregation kinetics with simultaneous multiple sample light scattering", Analytical Biochemistry, Elsevier, Amsterdam, NL, vol. 437, No. 2, Mar. 7, 2013 (Mar. 7, 2013), pp. 185-197.

Colin a. Mcfaul et al: "Simultaneous multiple sample light scattering detection of LCST during copolymer synthesis", Polymer, Elsevier Science Publishers B.V, GB, vol. 52, No. 21, Aug. 21, 2011 (Aug. 21, 2011), pp. 4825-4833.

* cited by examiner

CHARACTERIZATION OF POLYMER AND COLLOID SOLUTIONS

RELATED APPLICATIONS

This application claims priority to U.S. Provisional Application No. 61/868,050, filed 20 Aug. 2013, and to U.S. Provisional Application No. 62/002,111, filed 22 May 2014; both of which are hereby incorporated by reference in their entireties.

FIELD OF TECHNOLOGY

This specification is directed to improved systems and methods for characterization of polymer and colloid systems. Specifically, within the context of monitoring the light scattered by multiple independent samples, this specification describes a variety of stressors that can be applied to polymer and colloid solutions to test their stability and suitability for different applications.

BACKGROUND

Light scattering methods are useful for characterizing polymer and colloid solutions. Quantities, such as molar mass, spatial dimensions, shapes and interaction parameters can be measured by the intensity of scattered light. These measurements are often referred to as Static Light Scattering (SLS) measurements. Other types of light scattering, such as dynamic light scattering (DLS), auto-correlate scattered light to yield particle diffusion coefficients and other parameters. It is also possible to use SLS and/or DLS to monitor how properties of particles in solution change over time. It is noted that, strictly speaking, when colloids are involved they are normally termed to be in 'suspension' in a liquid since they do not dissolve in the usual sense and hence there is no 'colloid solution'. For convenience in this document, 'colloid solution' will be used to designate any liquid containing colloids, whether in suspension or otherwise.

Improved systems and methods for the characterization of polymer and colloid solutions are herein disclosed.

SUMMARY

This specification is directed to improved systems and methods for the characterization of polymer and colloid solutions.

The foregoing and other objects, features and advantages of the present disclosure will become more readily apparent from the following detailed description of exemplary embodiments as disclosed in this specification.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
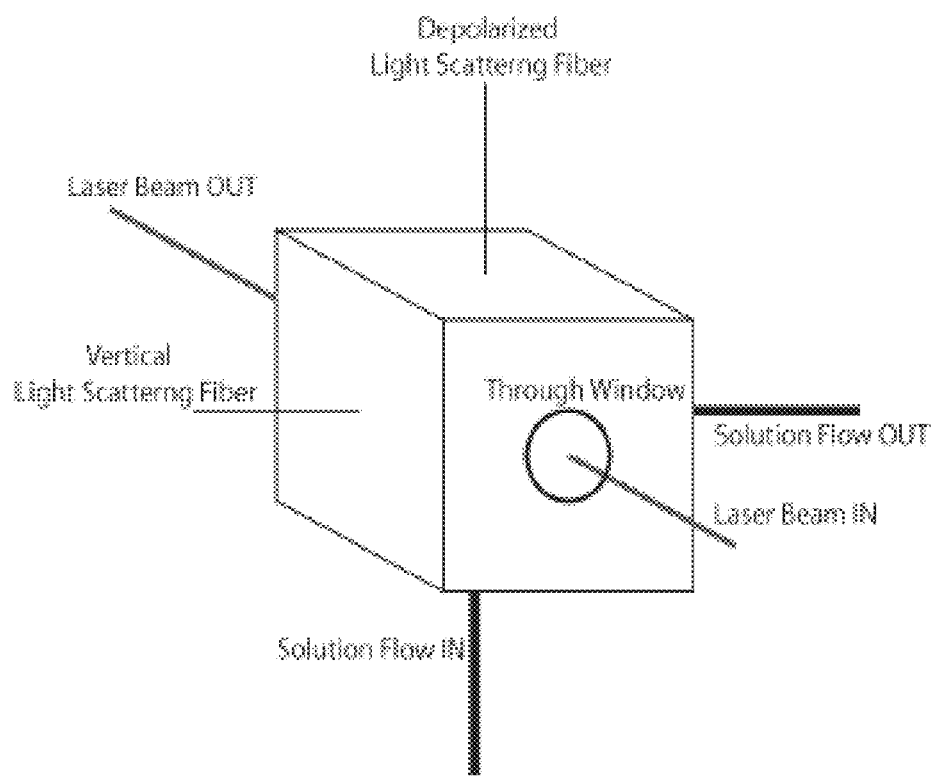
FIG. 1 illustrates a flow cell schematic of an exemplary SMSLS depolarized light scattering system.

It will be appreciated that for simplicity and clarity of illustration, where considered appropriate, reference numerals may or may not be repeated among the figures to indicate corresponding or analogous elements. In addition, numerous details are set forth in order to provide a thorough understanding of the example embodiments described herein. Example embodiments described herein may be practiced without certain details and elements, with additional details and elements or in combination with other embodiments described in this specification.

U.S. Pat. No. 6,653,150 titled "Automatic Mixing and Dilution Methods for Online Characterization of Equilibrium and Non-Equilibrium Properties of Solutions Containing Polymers and/or Colloids" by Reed is directed to the automatic, online dilution of polymer and/or colloid solutions such that, when the diluted polymer stream flows through suitable detectors, non-equilibrium processes such as polymerization, degradation and aggregation, can be monitored. U.S. Pat. No. 6,653,150 is incorporated by reference in its entirety for all purposes herein. The automatic continuous online monitoring of polymerization reactions (ACOMP) is enhanced by the current disclosed technology to allow solutions containing a high density of large scattering particles to be diluted sufficiently to enable the analysis of light scattering spikes (LSS). LSS occurs when large individual particles pass through the scattering volume $V_s$ and produce a spike or 'flash' of light much greater than that of any homogeneous background scattering that may be present due to a population of much smaller particles. For example, a single bacterium can scatter trillions of times more light than a single protein molecule. In some embodiment, one or more light scattering flow cells are fed with a dilute, conditioned liquid sample prepared automatically and continuously by the front end of an ACOMP system to enable LSS analysis.

U.S. Pat. No. 6,618,144 titled "Device and Method of Simultaneously Measuring the Light Scattering from Multiple Liquid Samples Containing Polymers and/or Colloids" to Reed is directed to Simultaneous Multiple Sample Light Scattering (SMSLS) devices, which allow independent light scattering measurements to be made independently and simultaneously on multiple samples. U.S. Pat. No. 6,618,144 is incorporated by reference in its entirety for all purposes herein. The SMLS approach dramatically increases throughput compared to single-sample instruments and also brings more economy per sample measured.

SMSLS takes advantages of the considerable advances of the past few decades in capabilities and lowered costs in the areas of lasers, fiber optics, light detection technology, and powerful microcomputing and programs to create instrumentation 'under one roof' allowing multiple light scattering experiments and monitoring to be carried out continuously and simultaneously, independently of each other. Light sources can include, but are not limited to lasers, particularly diode lasers due to their low cost and high stability. A variety of light detection methods are available, including but not limited to photomultipliers, photodiodes, and Charge Coupled Devices (CCD). CCD detection has distinct advantages in terms of low cost, high sensitivity and high signal to noise ratios.

Sample cells include the 'batch' type, in which a sample solution is introduced into a cell which resides in the incident light beam path or can be inserted into and removed from the beam path. Such cells can be round, square, hexagonal, octagonal or other shape. They can be filled automatically or manually. Flow cells allow the sample solution to flow through them during measurements. The liquid sample can re-circulate through the system using some pumping mechanism, or can flow into another detector or to waste without recirculation. SMSLS has important high throughput applications in many areas. SMSLS can be modified and implemented using specific SMSLS systems and methods tailored to characterize a variety of polymer and colloid solutions, including but not limited to polymer and colloid solutions characterized using the SMSLS technology described herein.

For example, biotechnology and pharmacy SMSLS systems and methods disclosed herein are capable of characterizing mutagenic and engineered protein type polymer and colloid solutions using high throughput, quantitative, continuous monitoring of the therapeutic protein stability in different formulations and from different mutagenic and engineered protein types. Instability in protein drug formulations (e.g. protein aggregation) is a major problem across the entire biotechnology and pharmaceutical industry. Biotechnology and pharmacy SMSLS systems and methods provide an extremely sensitive tool for monitoring, understanding, and mitigating instability occurring in the manufacture of protein drug formulations (e.g. protein aggregation).

Additionally, SMSLS systems and methods for the dissolution of polymers and colloids disclosed herein are capable of rapid rendering and determination of phase diagrams. Phase diagrams of systems with two or more components (e.g. water, salt, and surfactant) require much time and tedium to establish. SMSLS systems and methods for the dissolution of polymers and colloids disclosed herein provide a means of phase diagram building, including determining the area of 'micro-solubility' for sparingly soluble substances in different solvents.

SMSLS systems and methods for polymer stability testing disclosed herein are also capable of applying stressors to polymer or colloid solutions including heat stress, ultrasound, freeze/thaw cycles, shear stress and exposure to different substances and surfaces that create a polymer stress response used to characterize the polymer solution and stability. Substances to which the polymer can be exposed include different types of metals, ceramics, plastics, coatings, oil, a wide variety of ions, and gases, such as $O_2$, $N_2$, and more complex gases. Other stressors can include light and other forms of radiation. Freeze/thaw cycles of proteins, for example, are widely encountered in biotechnology, and the current disclosed technology allows for freezing and thawing samples within sample cells and immediately monitoring the samples behavior before, during, and after the freeze/thaw process. Yet other stressors can include light, including intense light, that may degrade or damage the polymer or colloid solutions. 'Light' includes any type of electromagnetic radiation from gamma rays through to radio waves. Ionizing radiation can also be used as a stressor, such as electron, proton, and ion beams, in addition to ionizing electromagnetic radiation. Stressors can also be applied to the surfaces of polymer and colloid solution instead of, or in addition to their application into the solution. One example is the monitoring of the difference of stirred protein behavior with a gas interface versus with a solid interface instead of gas. Additionally stressors include addition of materials during the monitoring process including titrants and other materials. For example during the monitoring process one can add additional materials, indiscrete amounts or continuously, that can change ionic strength, pH, metal ion content, and antigens, that may invoke responses in the polymer or colloid solutions, such as phase transitions, aggregation, disassociation, nano- or microstructuration, crystallization, etc. Such additions or titrations can cause measurable responses either immediately or over time. Among other effects, different stressors can lead to different kinetic pathways of instability or other time dependent processes in polymer and colloid solutions.

SMSLS systems and methods for sub-component characterization disclosed herein can also be used to monitor the generation of sub-components using automatic continuous online monitoring of polymerization reactions ("ACOMP"). Flowing reactor species and contents under different stimuli conditions are probed for responsive behavior using ACOMP.

SMSLS systems and methods for uptake and kinetics characterization disclosed herein can also be used to measure uptake and kinetics of a target agent by encapsulation agents. An example is oil uptake by encapsulators or dispersants that can be used in oil spills.

The presently disclosed technology is directed to the aforementioned and other improved SMSLS systems and methods, but is not limited to the fields of use or advantages enumerated herein.

SMSLS depolarized light scattering technologies herein disclosed can use linearly polarized incident laser light as the source to detect scattered light in one or more scattering planes. One or more detectors are arranged in the plane perpendicular to the linearly polarized light, where scattering from isotropically scattering particles is at a maximum. Typically the plane of polarization of the incident light is termed 'vertical' and the plane of maximum scattering for non-depolarizing scatterers is the horizontal plane. This horizontal plane is often referred to as 'the scattering plane' when vertically polarized incident light is used. In many applications of the present technology, such as for synthetic and biological polymers and colloids, the scattering mechanism will be via electric dipole scattering. Many scattering particles of interest have scalar electrical polarizability (which determines the size and direction of electric dipoles induced by incident light on the particle), which means that the scattered light is polarized in the same direction as the incident light. For instance, scattered light is vertically polarized for vertically polarized incident light.

Spatially anisotropic particles may have tensorial electrical polarizability, which means that scattered light is not necessarily in the polarization state of the incident light. Such scattered light includes depolarized scattered light. Tensorial polarizability frequently arises when a particle has anisotropic shape or morphology, such as rodlike, elliptical, disk, etc. It also occurs in many small molecules, such as toluene, carbon disulfide, methanol, and other small molecule liquids. The scattering analyses referred to in the vast majority of applications in the field assume that an incident light photon is scattered only once. Multiple scattering, such as in turbid media can also cause depolarized scattering components to occur, even when the scatterers themselves are isotropic and do not produce depolarized scattered light. For large isotropic particles, i.e. much larger than the wavelength of light, multiple internal scattering can likewise cause depolarized scattering.

SMSLS depolarized light scattering technologies herein disclosed measure depolarized scattering as a means of determining whether certain particles have tensorial polarizability and shape anisotropy. Monitoring changes in depolarized scattering over time can reveal whether scattering particles are undergoing morphological changes such as, fibrile-like aggregation of amyloid proteins which is linked to Alzheimers disease. Fibrile-like aggregation of amyloid proteins can be monitored by an increasing depolarized signal, while the usual in-scattering-plane detection can follow the net change in molar mass. Detection of depolarized scattering can also be used to assess levels of turbidity in a solution, since the depolarized scattering will increase as turbidity increases. Detection of depolarized scattering can also monitor the increase in size of particles, as particles larger than the wavelength of light, even morphologically isotropic ones, can cause depolarized scattering.

Various SMSLS embodiments for depolarized scattering detection can be used for batch cells and flow cells. There are several means of implementing depolarization detection in SMSLS technologies herein disclosed. By a polarization reciprocity relation, detecting the vertical scattering component from horizontally polarized incident light is equivalent to detecting the horizontally scattered component of vertically incident polarized light. Placing a half-wave plate in front of the laser will switch the incident polarization from vertical to horizontal and the photodetector used for 'normal scattering' detection in the scattering plane will measure the depolarized scattering. The half-wave plate approach can be used for both batch and flow cells. It can be automatically inserted and removed in various ways including, but not limited to a stepper motor or other device. Other devices that can achieve the rotation of plane of polarization include photoelastic modulators, Kerr cells, and Pockels cells. The term 'normal' detection refers to the scattered light normally detected in the horizontal scattering plane when no analyzing polarizers are inserted between the scattered light and the detection means. ('Normal' in this restricted usage does not mean 'perpendicular' or 'orthogonal' as is frequently meant in other contexts). In the case where there is no depolarized scattering the 'normal scattering' will be vertically polarized. If there is depolarization the 'normal scattering' will contain both polarized and depolarized components. The photodetectors destined for depolarized detection, on the other hand, measure only depolarized scattering. In some embodiments of the present technology it may be desirable to place an analyzing polarizer between the light scattered in the horizontal scattering plane and the detection means so that only the vertically scattered component of the 'normal scattering' in this case will be detected.

In most cases a photodiode, CCD (charge couple device) or other photodector, such as a photodiode or photomuliplier tube, can be placed directly in close proximity to the scattered light for detection. Such a detector will normally have whatever apertures, lenses or other optical components that may be necessary to detect light from only a desired portion of the incident beam within the sample cell. The illuminated portion of the beam inside the cell that is detected is customarily termed the 'scattering volume'. In many cases it is convenient to use optical fibers to gather light from the desired scattering volume and lead it to a photodector, such as a photodiode or CCD. In all cases and drawings where 'optical fibers' are referred to, it is understood that direct photodetection can also be used, and optical fibers are not a requirement. One advantage of fiber optics in an SMSLS instrument is that multiple optical fibers from multiple optical cells can be lead to a single CCD, or to multiple CCDs whose total number is much less than the number of fibers. With the low cost and miniaturization of photodiodes and other photodetectors, however, there can be convenient SMSLS instruments in which each cell may be equipped with its own photodetectors instead of optical fibers.

In another embodiment of SMSLS depolarized light scattering systems and methods for batch cells, a second detection fiber is placed at the bottom or top of the cell, allowing the same reciprocity relation to work, where now the fiber at the bottom or top of the cell is at 90 degrees to the usual horizontal scattering plane. This positioning of the detection fiber allows for measurement of depolarized scattering by, while, simultaneously, the normal scattering can be measured by a separate photodetector in the horizontal scattering plane.

The vertical component of scattered light is detected using stray light minimization steps. Stray light is light which enters the scattered light detector from sources other than the desired scattering particles such as, light that 'flares out' from interfaces (e.g., air/glass, liquid/air, liquid/glass). For scattering cells using fiber optic detection the fiber can be pulled into a cylindrical tube such that the acceptance angle of the fiber is determined by its depth within the tube rather than by the numerical aperture of the fiber, which governs the light taken in if there is no recessing of the fiber optic (e.g., a fiber mounted flush to the bore of a scattering cell, immersed in liquid). In a batch cell, stray light from reflections at the meniscus may occur. This may be reduced by contacting a black or dark material with the liquid surface that can reduce reflection. Black or dark materials can include a flat, black plastic disk which fits the internal diameter of the cell.

In the case of flow cells, a detector at 90 degrees to the usual horizontal scattering plane can also be used. The flow path should be such that an optical fiber or other means of photodection can be inserted in the top or the bottom of the flow cell.

FIG. 1 illustrates a flow cell schematic of an exemplary SMSLS depolarized light scattering system according to some embodiments.

In any of the aforementioned SMSLS depolarized light scattering systems and methods, the performance of the depolarization detection system can be assessed using depolarization ratios of organic solvents that are well known (e.g. toluene, carbon disulfide, etc.). The extinction of the polarized component compared to the depolarized component can be used to determine performance. When an isotropic scatterer is used, such as a latex sphere of diameter <10 nm, a very high performance system having as little as 10 as the ratio of depolarized (e.g. leakage in this case) to polarized signal can be achieved. In principle, the small latex spheres will not depolarize the incident light upon scattering.

Figure 2A:
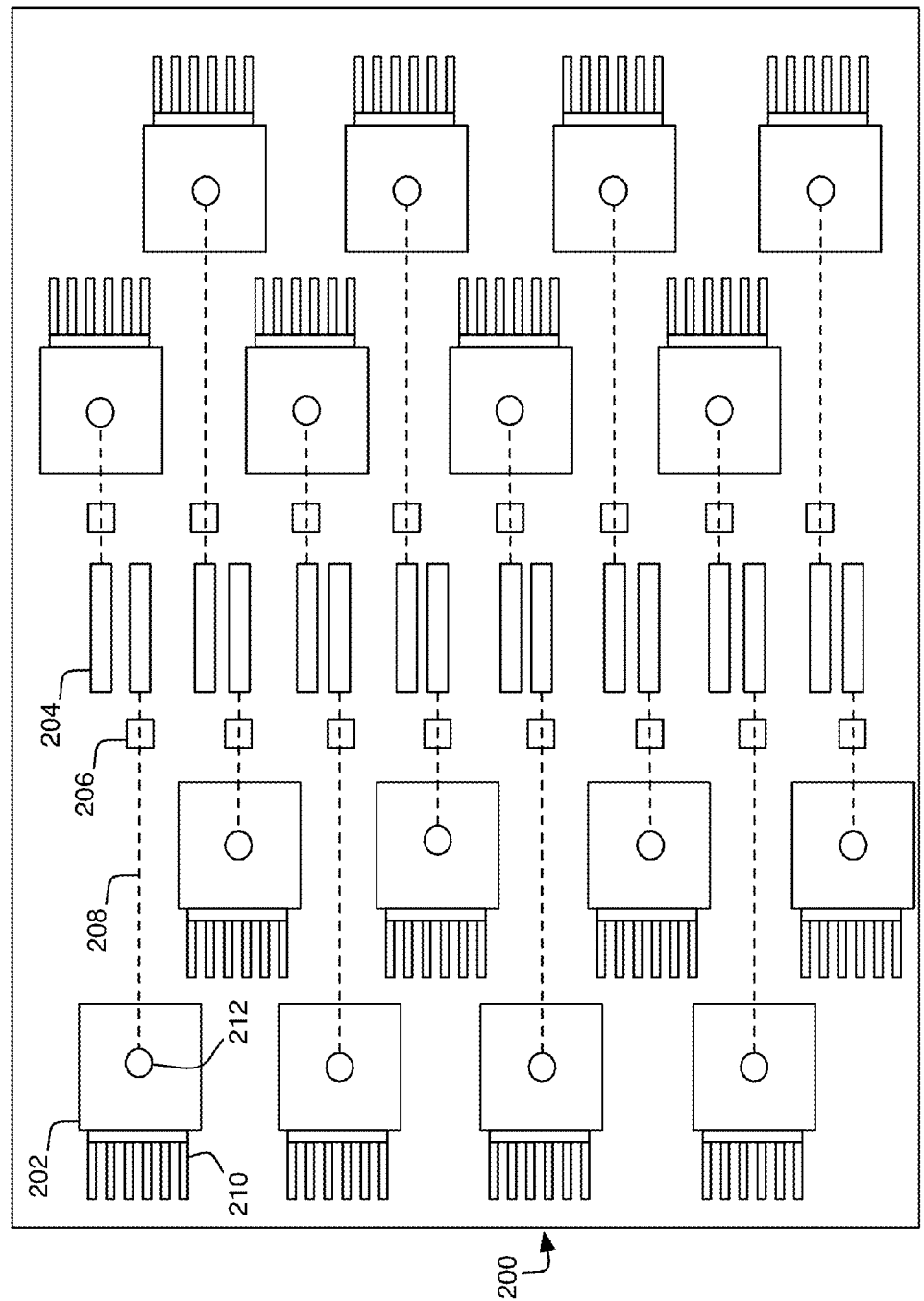
FIG. 2A-2C illustrate an example SMSLS system for the characterization of polymer and colloid solutions.
Figure 2B:
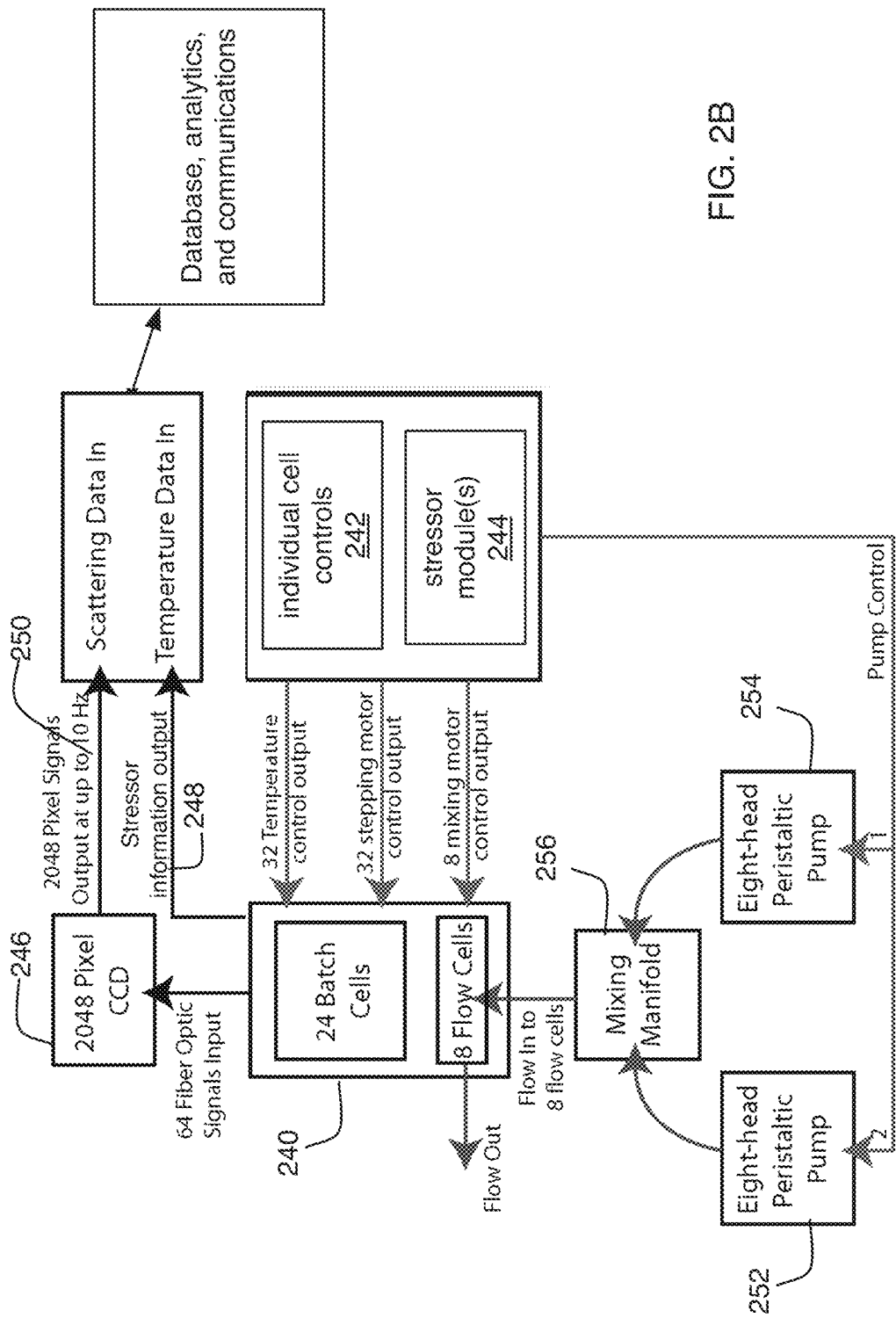
Figure 2C:
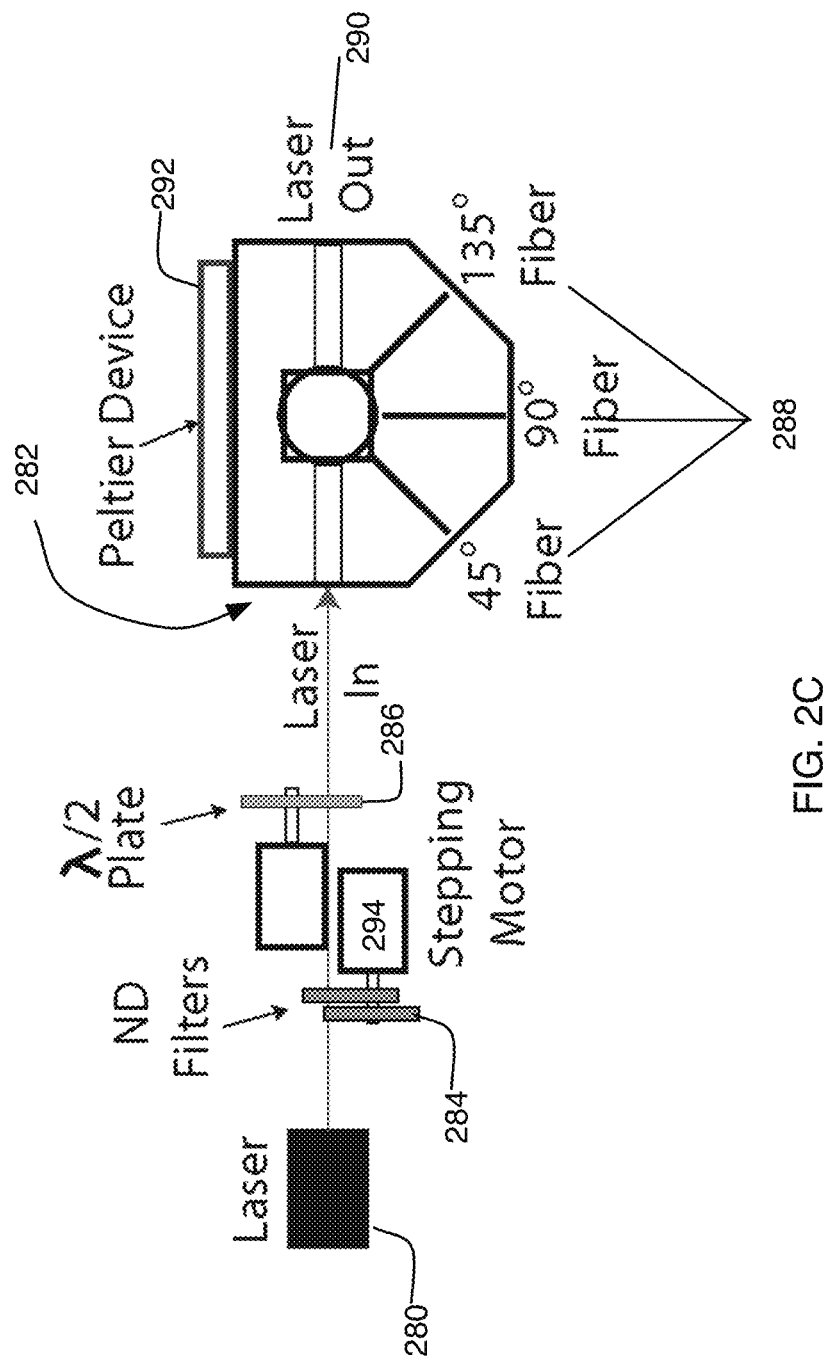

FIG. 2A-2C illustrate an example SMSLS system for the characterization of polymer and colloid solutions according to some embodiments. FIG. 2A illustrates an example SMSLS apparatus 200. As depicted in FIG. 2A, there are sixteen SMSLS cells 202. In some embodiments the number of SMSLS cells 202 may vary to be greater or less than sixteen. In some embodiments the interior of the SMSLS cell can be square. One of ordinary skill in the art will appreciate that many variations of the interior SMSLS cell shape can be used without parting from the spirit of the disclosed technology. The SMSLS cells 202 are coupled to one or temperature control devices 210 capable of controlled or uncontrolled heating of the SMSLS cell. In some embodiments a peltier device is used in the temperature control configuration to also allow cooling of the SMSLS cell 210, or a resistance heating unit, such as a high resistance wire, etc. In some embodiments, in addition to the peltier device each SMSLS cell can also be coupled to a fan to exhaust heat extracted from the SMSLS cell.

Each SMSLS cell is configured to receive light from a light source, such as a laser 204. The laser 204 is positioned to emit laser light 208 into the cell 202. The laser light 208 may pass through neutral density filters 206 to regulate the intensity of laser light entering the cell 202. In some embodiments, fiber optics 212 in the SMSLS cell transmits the laser light emitted into the cell to a photodector (not shown). In some embodiments the photodetector may be a charged couple device (CCD), a photomultiplier, a photodiode, etc.

FIG. 2B illustrates an example schematic for high performance SMSLS. The SMSLS cells 240 can either be batch cells or flow cells. In a flow cell, fluid flows through the cell while laser light emitted into the cell flows through a portion of the flowing fluid stream. Peristaltic pumps 252, 254 can be utilized to pump different materials into a mixing manifold 256 to mix different materials prior to flowing the materials through the flow cell. For example, peristaltic pump 252 may pump a protein into the mixing manifold and an alternative peristaltic pump 254 can pump buffer into the mixing manifold 256 producing a mixed stream of protein and buffer exiting the mixing manifold 256 and entering into the flow cell 240. One of ordinary skill in the art will appreciate that other pump types may be used in conjunction the flow cells and mixing manifolds. For example, in some embodiments a positive displacement pump may be used to pump materials into the mixing manifold. In a batch cell, the composition of material within the batch cell is prepared independently and individually introduced into each batch cell in a vessel such as an optical glass cuvette or other similar vessel. In some embodiments, the SMSLS cells may be batch cells, flow cells, or a combination of batch and flow cells.

In some embodiments, the SMSLS system can include individual cell controls 242 configured to set up the samples within the individual cells. The individual cell controls can include software components including a user interface for receiving instructions from an operator regarding the setup and variables tested among the individual cells. In some embodiments, the individual cell controls 242 can also include an interface to designate sampling statistics and intervals of interest. In some embodiments the individual cell controls can also control inputs into the cell for providing material to the cells.

In some embodiments, the stressor module(s) 244 control the stressors associated with each individual cell. In some embodiments the stressors can include, but are not limited to change in temperature, including freezing and thawing, application of shear forces, introduction of certain surfaces, such as metals, plastics, gas bubbles, glass, oils, specific ions, chelating or other chemical agents, ultrasound, light and other forms of radiation. The stressor module(s) 244 allows for the temperature, stirring, stepper motor, and other stressors associated with each cell to be controlled individually for each cell. In some embodiments, the stressor module is a combination of software and hardware such as computer code for controlling a stepper motor, a processor for interpreting the computing code, the stepper motor hardware for creating a magnetic field about a cell, and a magnetic stirrer within the cell—collectively these all can be considered parts of a given stressor module. Other stressor modules include software, computing devices, and other instruments for introducing a stressor whether it is a form of energy, material, or any other stressor identified herein or known to those of ordinary skill in the art.

Light scattering measurement associated with the effects of the stressor introduced to the SMSLS cell is detected by a photodector 246. In some embodiments, the photodetector 246 can be a charged couple device (CCD). In some embodiments, the CCD can have 2048 pixels, but the present technology isn't limited to CCDs of a particular pixel count. Any photodetector that can measure reflected light in a sample can be used, as will be understood by those of ordinary skill in the art. The light emitted from each laser can be transmitted to a photodector 246 through fiber optics present in each individual sample cell or a photodector can be coupled to each sample cell. Additional outputs associated with each cell may be measured such as the sample temperature, stirring motor speed, gas flow into the sample, liquid flow into the sample, etc. as indicated by stressor information output 248. Light scattering data 250 and stressor information output data 248 are captured in a database that performs various forms of data analytics to determine how the stressors affect the characterization of the polymer and colloid solutions.

FIG. 2C illustrates an example configuration of an SMSLS cell. A laser 280 is configured to emit light into a SMSLS cell 282. In some embodiments neutral density (ND) filters 284 are utilized to regulate the intensity of laser light emitted into the SMSLS cell 282. The half-wave ($\lambda/2$) plate 286 through which the laser 280 light can pass through can switch the incident polarization from vertical to horizontal and the photodetector used for 'normal scattering' detection in the scattering plane will measure the depolarized scattering. The half-wave plate approach can be used for both batch and flow cells. Fiber optics 288 within the SMSLS cell are used to transmit laser light emitted from the laser to a photodetector device. In some embodiments the fiber optics 288 are positioned at one or more angles desired, such as 45°, 90° or 135° to capture laser light scattered at each angle. One of ordinary skill in the art will appreciate that fiber optics 288 may be positioned at other angles to capture laser light scattered. Laser light that travels out of the SMSLS cell 290 is disseminated to a laser trap. The peltier device 292 is utilized for cooling and a separate heating element is utilized for heating. A temperature control device can be set to regulate the temperature of the SMSLS sample cell. The stepper motor 294 is coupled to a magnet which creates a magnetic field within the SMSLS. As the stepper motor 294 rotates at a given revolution per minute (RPM), the magnetic field is changed within the cell which in turn rotates a magnetic stir bar within the SMSLS cell at the specified RPM.

In some embodiments other devices and modules can be used along with the SMSLS system described above to provide additional measurements, or analysis. For example an autocorrelation module for Dynamic Light Scattering, optical bandpass filters for measuring fluorescence, or highly attenuated throughput beams can be used for measuring turbidity.

While the above figures, have been described with some specificity above, persons of ordinary skill in the art will appreciate many variations to the actual system components and layout thereof and still remain within the scope of the present technology. None of the disclosure herein is intended as limiting unless specified by the appended claims.

Stirring in SMSLS

In some embodiments of the present technology, a polymer, protein or colloidal solution is subjected to one or more stressors to initiate or trigger one or more time dependent responses or processes, such as aggregation, degradation, phase changes, solubility changes. Stressors can include, but are not limited to change in temperature, including freezing and thawing, application of shear forces, introduction of certain surfaces, such as metals, plastics, gas bubbles, glass, oils, specific ions, chelating or other chemical agents, ultrasound, light and other forms of radiation.

Stressors can affect a given polymer or colloid solution uniformly throughout, but it is also possible that the stressors can be stochastic and have various origins and affect a given polymer or colloid solution inhomogeneously in space. For example, nucleation can be triggered around a nucleating particle in a particular volume element of a solution. The nucleation can proceed at some nucleation rate, fast or slow, through the rest of the solution. In typical light scattering, the 'scattering volume' refers to that portion of the illuminated sample detected by the scattering detection means. For example, a typical scattering volume involves a length of a laser beam passing through a solution defined by a field stop of some sort, such as a pinhole, aperture, photosensitive area, etc. Typical scattering volumes can be on the order of 10 nanoliters, wheareas the total solution volume may be on the order of 1 ml. In such a case, the scattering volume represents only $10^{-5}$ of the total sample volume. Hence, if a localized phenomenon, such as a nucleation event, occurs in only a few locations, it may not be detected in the scattering volume. In time, the nucleating site may diffuse in and out of the scattering volume, giving a rising LS (light scattering) intensity, followed by a declining LS intensity.

Exemplary SMSLS technologies disclosed herein are capable of avoiding sporadic and irreproducible detection of polymer or colloidal behavior. One means to achieve this is that the scattering volume can be increased to more accurately detect and characterize localized phenomenon occurring in a polymer or colloidal solution. For example, the size of a field stop can be increased with the use of an optical fiber or optical device with a larger numerical aperture and/or core diameter.

More than one scattering volume can also be used to more accurately detect and characterize localized phenomenon occurring in a polymer or colloidal solution. For example, more than one scattering volume can be created by splitting the incident beam and providing a detector for each portion of the split beam passing through the sample solution.

To more accurately detect and characterize localized phenomenon occurring in a polymer or colloidal solution, the SMSLS systems herein disclosed can raster the sample cell by moving the cell or incident beam in a particular pattern. The sampling cell can be automatically raised, lowered or moved from side to side with a device such as a stepper motor. The sampling cell can be moved in any pattern through an incidence beam from a laser or other source or the incidence beam itself can be moved in any pattern through the sampling cell by moving the light source. Raster can occur without moving the sample cell holder. Horizontal raster can be achieved, if desired, by enlarging the size of the sample cell holder and allowing automatic horizontal motion of the sample cell within the holder. The entire sample cell holder can also be moved with the sample cell fixed within it.

To more accurately detect and characterize localized phenomenon occurring in a polymer or colloidal solution, the SMSLS systems herein disclosed can provide minimally convective agitation to the liquid in the cell so that there is mixing of all sample cell volumes on a time scale sufficiently short when compared to any time dependent process, such as nucleation localized aggregation. The agitation applied to the polymer or colloidal is sufficiently low so that no significant shear stress capable of causing solution instability is introduced. Under sufficient shear, proteins may aggregate, polymers may be cleaved, colloids may flocculate. Therefore, minimally convective agitation is introduced.

In some embodiments, minimally convective agitation is a magnitude of agitation capable of mixing sample cell contents on a time scale less than the time dependent changes being measured in the solution but low enough to prevent introduction of shear forces that themselves can cause detectable changes in the solution.

In some embodiments, minimally convective agitation is provided with the use of a magnetic stir bar, or a mechanically inserted stirring blade attached to a stepper motor capable of extremely low rpm operation. The stepper motor is capable of rotating a stir rod or blade at 200 steps per revolution. This motor combined with the appropriate stepper driver will allow for smooth rotation at very low speeds, at 1 RPM and lower, RPM but also allows for higher rotation speeds up to 5,000 RPM or more.

The minimally convective feature can be tested as follows. When a single latex sphere (e.g. 2 μm diameter) passes through the scattering volume it produces a scattering spike. Ultra-dilute spheres can be introduced for detection with and without minimal convection. Since the scattering volume is tens of thousands of times less than the total cell volume, the dilution can be arranged to have a low probability of a sphere being in the scattering volume at any time. Without convection, spheres will linger in the scattering volume for a relatively long time once they diffusively enter, but the sphere will spend very long times between successive entries into the volume. With even minimal convection, spheres will be swept quickly through the volume, yielding sharp scattering peaks, and appear more frequently than by mere diffusion. In the limit of long sampling time, the total residence time of a sphere in the scattering volume will be the same by diffusion and convection, but the individual average residence time by diffusion will be much longer than by convection. The frequency of appearances in the scattering volume will be much higher by convection. A minimally convective agitation will allow for statistical computations and corresponding quantitative assessment of the performance of the minimally convective system.

The effect of shear stress, such as can be produced by stirring, is an important parameter to quantify in assessing stability of polymer or colloid solutions. In some embodiments, it is desirable to have controllable stirring stress, but having controllable stirring stress is not limiting. An agitation device capable of creating stirring stress within the polymer or colloid solution is used to agitate the solution over time.

In some embodiments, a stepper motor connected to an agitation device is used to produce stirring stress of the solution related to the rotation frequency of the device. The stepper motor can enable control of the stirring rate.

Even when accurate knowledge of the stirring stress applied to the solution is not available, the effect of shear stress on polymer or colloid solution stability is an important parameter to quantify. In some embodiments, a dc motor coupled to a magnetic or direct mechanical agitation means can be used to agitate the polymer or colloid solution to determine the stability of the solution.

Exemplary SMSLS Systems

An exemplary SMSLS system was manufactured comprising eight independent batch cells, each with a 35 mW vertically polarized red diode laser, a fiber optic to detect light scattering at 90 degrees, coupled to a CCD detector. Light scattering signals from all the cells gathered from the optical fibers from the sample cell holders are lead to and captured by the CCD, and are transmitted to a single computer for storage and analysis. Each sample cell has independent temperature control, which can be held constant, changed continuously or changed in steps. Stirring is provided by a magnetic stir bar in each cell, driven by a D.C. motor. Data sampling generally was conducted at 1 Hz, but slower sampling, e.g. 0.016 Hz was used for experiments lasting many hours. The system is described in Michael F. Drenski, Mark L. Brader, Roy W. Alston, Wayne F. Reed "Monitoring Protein Aggregation Kinetics with Simultaneous Multiple Sample Light Scattering (SMSLS): Application to High-Concentration Formulations." Analytical Biochemistry, 437, 185-197, 2013, which is herein incorporated by reference in its entirety for all purposes.

The effect of mechanical agitation stress is an important parameter to quantify in assessing stability of polymer or colloid solutions. In some embodiments, it is desirable to have controllable mechanical agitation stress. An agitation device capable of creating agitation stress within the polymer or colloid solution is used to agitate the solution and measure the local and average shear rate of solution over time.

In some embodiments, a stepper motor connected to an agitation device, which causes rotational stirring within the sample liquid, is used measure or estimate local and average shear rates of the solution based on the rotation frequency of the device. The stepper motor can enable precise control of the rate or magnitude of agitation. Other forms of mechanical agitation include shaking, bubbling gas through a solution, and applying non-periodic agitation such as caused by dropping or short term high acceleration or deceleration; e.g. as can occur in a commercial situation when a container of polymer of colloid, such as a therapeutic protein solution, is dropped.

Even when an accurate estimate of agitation stress, such as stirring stress, applied to the solution is not available, the effect of unmeasured levels of stirring stress on polymer or colloid solution stability is an important parameter to quantify. In some embodiments, a dc motor coupled to a magnetic or direct mechanical agitation means can be used to agitate the polymer or colloid solution to determine the stability of the solution.

Experimental Results of SMSLS Stirring on Some Proteins

Figure 3:
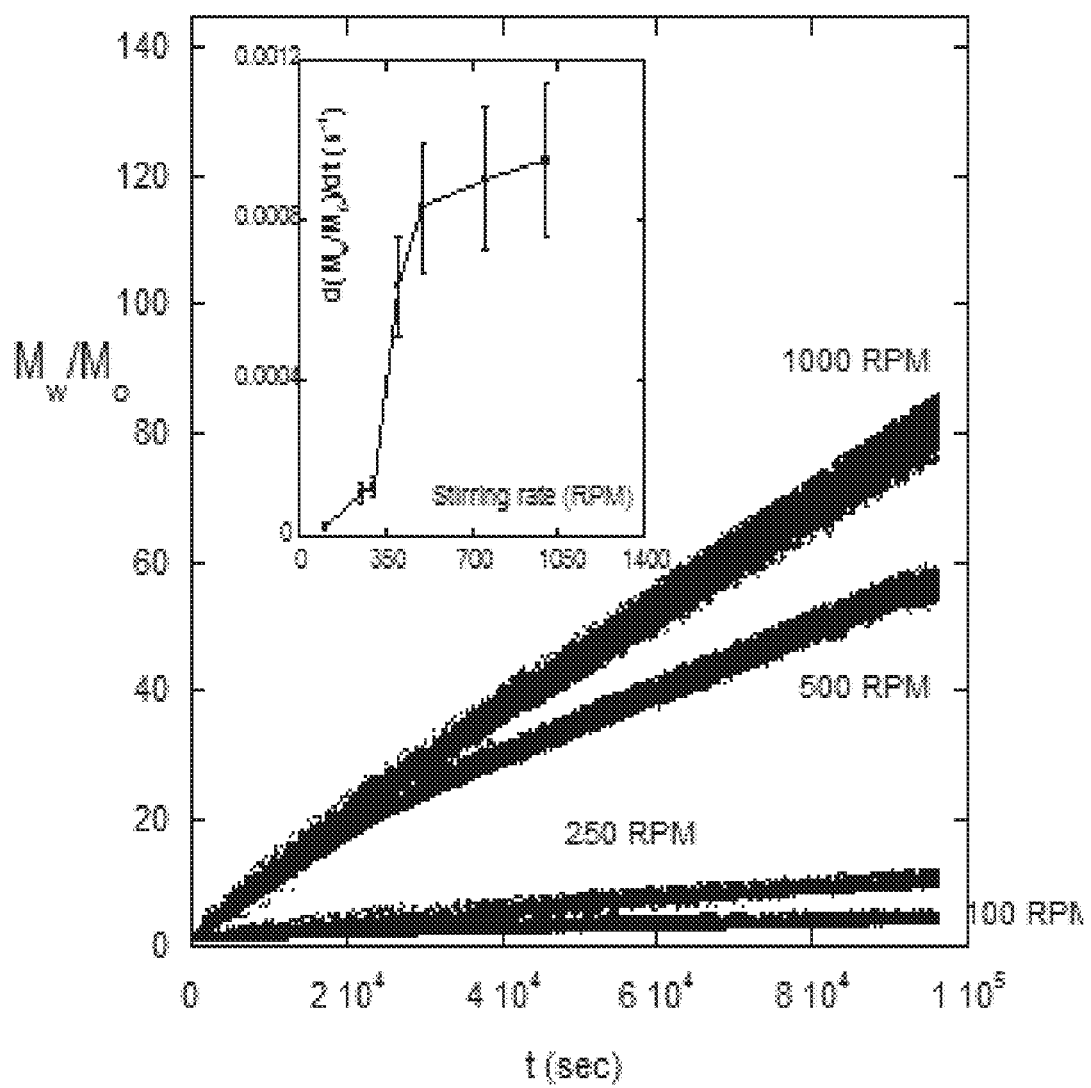
FIG. 3 illustrates a plot of time dependent data for stir-induced aggregation of a protein for stirring from 100 RPM to 1,000 RPM.

FIG. 3 shows time dependent data for stir-induced aggregation of a protein for stirring from 100 RPM to 1,000 RPM. The inset shows the initial linear aggregation rate $d(M_w/M_0)/dt$ vs RPM. The aggregation rate increases as stir rate RPMs increases. The inset to FIG. 3 shows a sigmoidal dependence of aggregation rate on RPM. The means of determining aggregation rate is that of Drenski, Alston, Brader, and Reed: $M_w/M_0$ is measured using SMSLS by forming the ratio of the scattered intensity at any moment minus the solvent scattering baseline divided by the initial scattered intensity at t=0 for the protein solution minus the solvent baseline scattering. $M_w/M_0$ represents the fractional change of the weight average mass of all non-aggregated and aggregated proteins in solution to the weight average mass at t=0. For aggregation $M_w/M_0$ increases with time and the slope of the early linear portion of the SMSLS scattering data is $d(M_w/M_0)/dt$, and represents the aggregation rate in terms of fractional increase of aggregate weight average weight per second. The inset to FIG. 3 shows the rates obtained from the early linear slopes of data such as shown in the main portion of FIG. 3.

Figure 4:
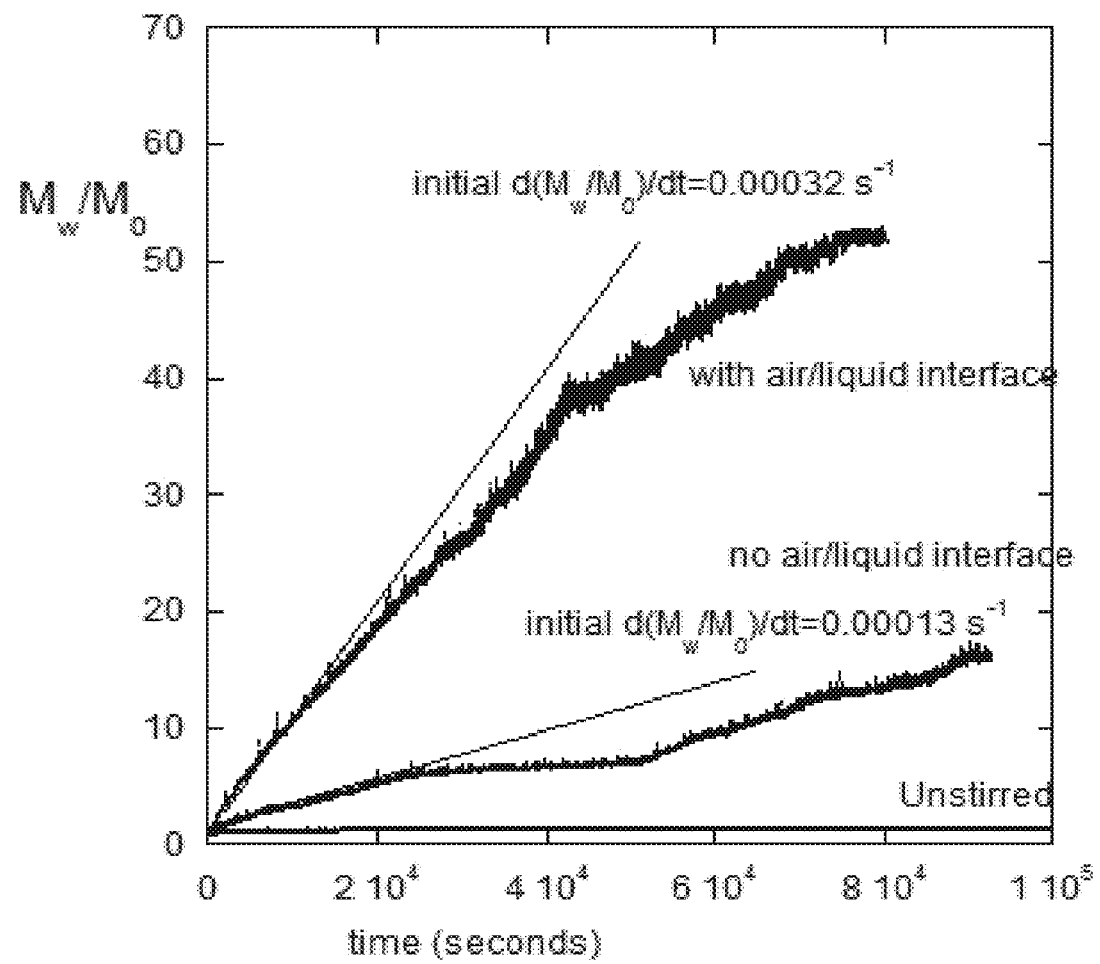
FIG. 4 illustrates a plot of aggregation data for a protein at 35° C. stirred at 500 RPM.

Bee et al., and others, have found that protein aggregation due to stirring can sometimes be traced to increased exposure of the proteins to the air interface, rather than the mechanical shear stress of stirring. SMSLS allows testing this by filling the vials up to the cap where there is no longer a liquid/gas interface. FIG. 4 shows aggregation data for the same protein as FIG. 3 when at 35 C and stirred at 500 RPM. Shown in FIG. 4 is data for a sample with the air/liquid interface ('uncapped') and data for a sample without the air/liquid interface ('capped'). The aggregation rate in the capped case is two and a half times slower than the uncapped case. Hence, the air/liquid interface leads to more rapid aggregation kinetics, and removing it slows down but does not halt the aggregation process, suggesting that both the mechanical shear from stirring and the increased exposure to the air/liquid interface are stressors. Also shown is a control sample in which there was no stirring; no aggregation occurred on the time scale of the experiment. While different proteins were found to have orders of magnitude difference in thermally induced aggregation, the same proteins have very similar aggregation rates under stirring, suggesting that a different damage mechanism is in effect under stirring, which is different from thermally induced unfolding. The capability to make such distinctions between different interfacial stresses may represent a convenient approach applicable to evaluating protein candidate molecules and trial formulations early in development for relative susceptibility to processing stresses.

Varying Formulation Conditions and Formulation Conditions as Stressors

An important application of SMSLS is in developing formulations, where the goal is to optimize such factors as excipients, pH, ionic strength, concentrations, etc. The formulation conditions themselves are both stressors and affect how the formulation reacts to other stressors, such as temperature and stirring. These must usually be worked through empirically to find the best choice. The ability of SMSLS to simultaneously monitor multiple samples, as well as the ability to titrate samples with different agents while monitoring in realtime, will increase formulation screening throughput enormously.

Figure 5:
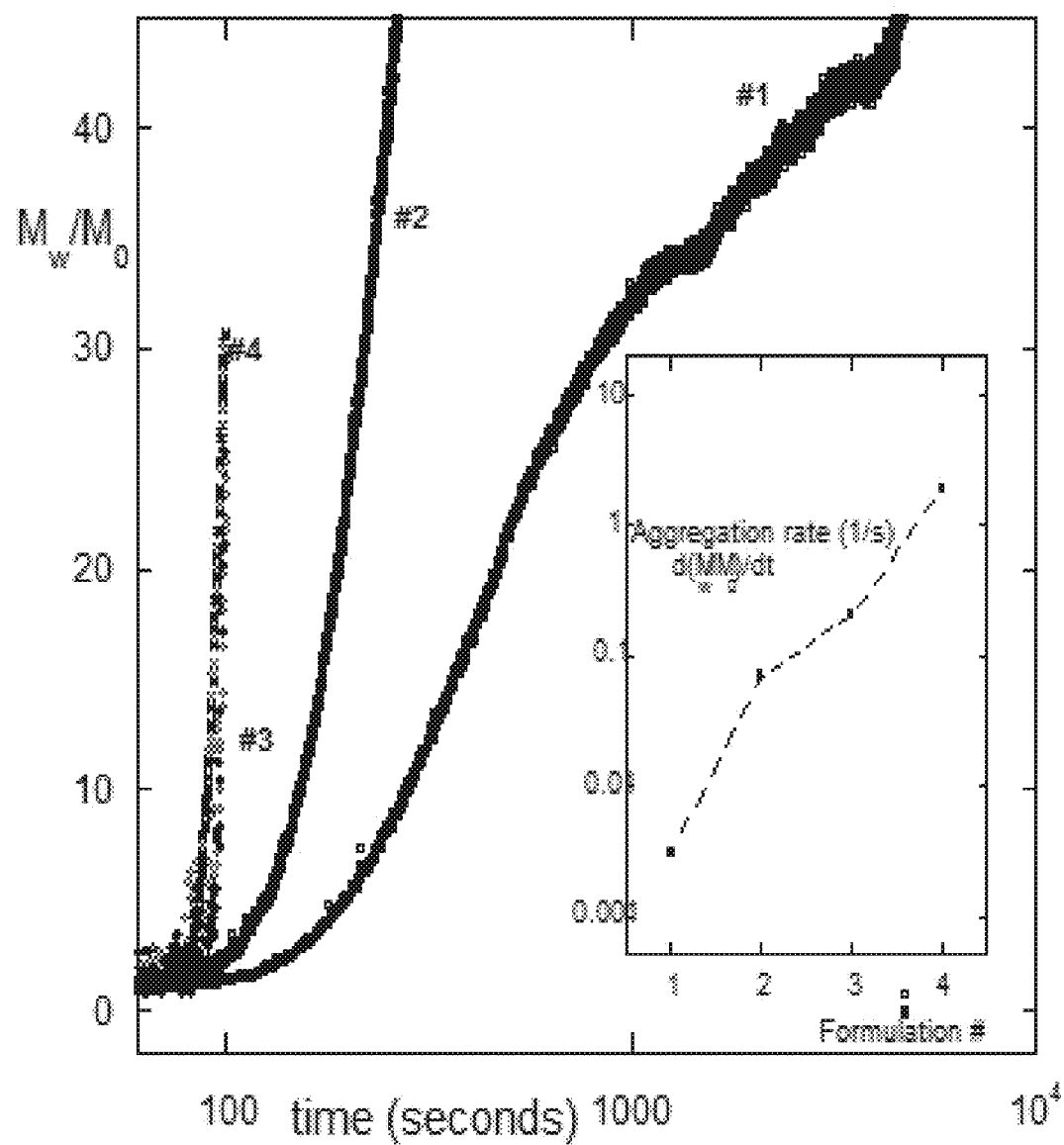
FIG. 5 illustrates a plot of the aggregation behavior of mAbC at 60° C., without stirring, at a concentration of 0.001 g/cm$^3$, for four different formulations which vary in pH and ionic strength.

FIG. 5 shows the aggregation behavior of mAbC at T=60 C, without stirring, at a concentration of 0.001 g/cm$^3$, for four different formulations which vary in pH and ionic strength. As seen, the differences in stability due to formulation conditions are dramatic, so much so that a logarithmic time scale is needed to appreciate the different aggregation rates. The inset to FIG. 5 shows the aggregation rate, $d(M_w/M_0)/dt$ vs formulation #. There is over a six hundred fold difference in rate between the most stable and least stable formulations.

Selectable Attenuation Devices for Incident Light

In some embodiments of a SMSLS device can further include an automatic light modulation system for automatically monitoring, attenuating and controlling the intensity of the incident light beam or other light beam in the SMSLS systems and methods herein described. The automatic light modulation system can include a controller or processor; a plurality of neutral density filters arranged on movable member; a means for configuring the filters, such as a drive train, motor or other mechanical and/or electrical device coupled to movable member; a photodector e.g., a CCD or photodiode, etc. coupled to the controller or processor for detecting the incident light. The controller or processor can send signals to the means for configuring the filters in response to the detected intensity of the incident light. The controller or a processor operating in a computer system can run analysis and control software for continuously and automatically monitoring incident light intensity and provide control signals to the configuration means to position the filters in appropriate filter configurations in the path of the incident light to modulate or attenuate the light as needed. While neutral density filters (i.e. those optical elements that attenuate transmitted light independently of the incident wavelength) are inexpensive and convenient for use, other items, such as plates of glass (e.g. microscope slides or slide covers) can be used to attenuate the light, as well as beam splitters, or optical filters tuned to specific wavelengths or wavelength ranges, etc, can be used.

Figure 6:
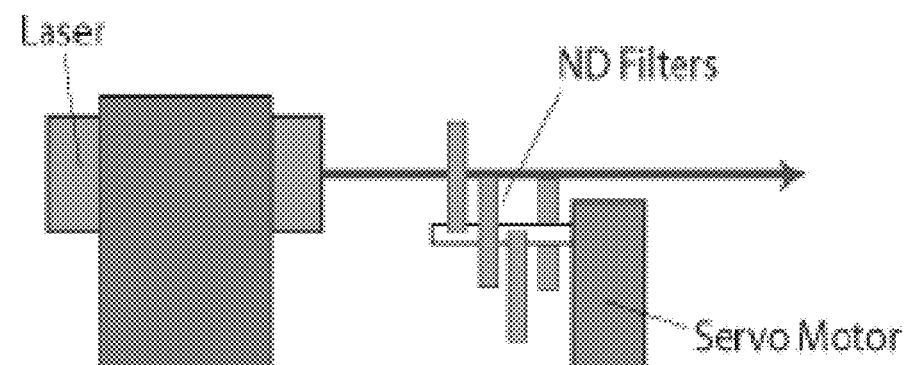
FIG. 6 illustrates a diagram of automatic light filtration elements.
Figure 6:
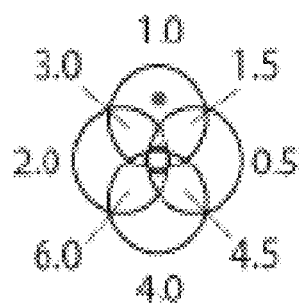

The automatic light attenuation element described above increases the range over which the input laser beam can be modulated. In some embodiments, the automatic light attenuation element is controlled automatically and the different filters are put into place with servo motors. The Filter fly wheel illustrated in FIG. 6 is one example embodiment of the automatic filtration elements described in this specification but is not limiting. Light attenuation devices can also be mounted linearly and actuated to move into position automatically with any sort of linear translation stage. It is also possible to use a single, continuous neutral density filter, either circular or linear, which allows a continuum of attenuations from nearly 0 to nearly 100% to be achieved by continuously moving around (circular device) or along (linear device) the attenuation device.

Extended Dynamic Range (EDR)

Because they are stable and inexpensive current SMSLS prototypes use 35 mW diode lasers. This power allows good signals from even weakly scattering solutions. As discussed herein above, neutral density filters must often be inserted into the beam path to reduce incident light power when highly scattering systems, such as protein aggregates, are measured. If the incident power is not reduced in such situations the central pixels of the CCD will saturate (or a photodiode or other detector could also saturate).

Another way to reduce pixel saturation is to reduce the integration time on the CCD, which is equivalent to a sensitivity control. Even in this case, however, where the central pixel is just below saturation, there is a certain dynamic range associated with any given pixel running from its low signal noise level up to the maximum value.

Figure 7:
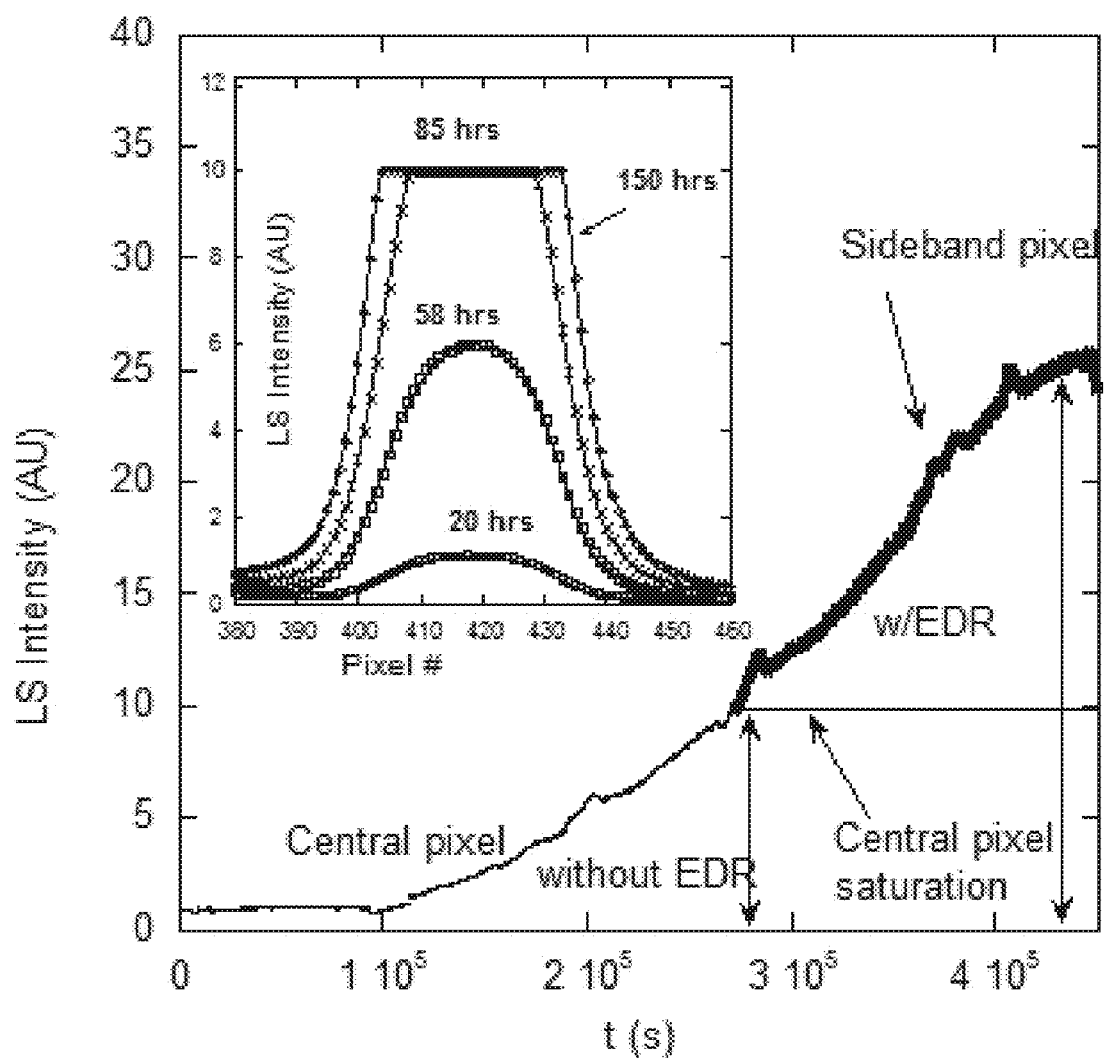
FIG. 7 illustrates a plot of a Gaussian intensity profile which shows how use of a sideband pixel has extended the dynamic range by approximately 150%.

In an exemplary method of extending the SMSLS dynamic range two features of the fiber optic that transmits the scattered light to the CCD are used i) CCD's as commercially available (Mightex TCE-1304-U, Alphalas CCD-S3600-D) have extremely linear response over their operating range, and ii) the light exiting from the fiber optic transmitting the scattered light to the CCD produces an approximately Gaussian intensity profile across the pixel range for each separate fiber. This allows 'roll-off' from saturated central pixels onto side pixels and continues linear and non-saturated detection over a much greater range of intensity that is possible by monitoring a single pixel or integrating the entire Gaussian intensity profile seen in the inset of FIG. 7. The main portion of FIG. 7 shows how use of a sideband pixel has extended the range by about 150%. Even higher gains can be made by using further rolloff pixels.

The data were taken from a current prototype. The intensity incident upon a group of pixels for a given fiber will vary over a wide range, being most intense at the center. FIG. 7 shows a factor of 2.5 increase in range by scaling pixel 396 to peak pixel 419. By the time 419 saturates at LS=10, scaled pixel 396 continues up to 25 before the scattering maximum for the sample is reached; a 2.5 fold increase in EDR is achieved. The experiment involved protein aggregation over a period of 5.2 days. The current PT2 cannot normally use EDR because of pixel cross-talk on adjacent fibers; i.e. light from one fiber overlapping outer pixels of the next. The data were obtained by employing extremely low scattering buffers (used for long term monitoring of protein buffer stability) in adjacent sample cells.

In some embodiments, a plurality of optical fibers is provided. The optical fibers transmit scattered light from sample-containing sample cells optically coupled to a CCD by means of a coupling device. The coupling device can be a mechanical device that holds the fibers in fixed positions with respect to the pixel array in the CCD. A plurality of pixels is assigned to the given fiber whose transmitted light reaches the pixels. A computer including a processor and software can be used to read some or all of the pixels on the CCD, groups of which are assigned, as mentioned, to each fiber. In an experiment a purpose-written software program will take the highest non-saturated signal at the beginning of an experiment, or a sub-group of non-saturated pixels at the beginning of the experiment. If during the experiment the scattering signal increases, for example due to the aggregation of polymers or colloids, and the chosen pixel or range of pixels becomes saturated, the program will automatically shift measurement to one of the next available non-saturated pixels. The initial highest or near-highest pixel or groups of pixels is known from the outset because: (1) the CCD is linear and (2) the ratio of intensity of each pixel in the group of pixels assigned to each fiber is known—i.e. the relative sensitivity of each pixel is known and measurement shifts smoothly to the next non-saturated pixel or group of pixels. If intensity continues to increase, this process of rolling off the currently saturated pixels to non-saturated ones, with the linear ratio of intensities to calibrate the rollover, can continue as many times as needed until the last pixel associated with a given fiber is reached. The result of this is a continuous record of scattering intensity for a given cell over a much greater intensity range than would be available if only a single pixel or subgroup of pixels were used and said pixel(s) saturated during the measurements.

Rollovers can be facilitated in a variety of ways and the above described procedure is not intended to limit the scope of this disclosure and method of rolling off saturated pixels. For example, it is not necessary to rollover to the next available unsaturated or group of unsaturated pixels. It may be desirable to rollover to pixels further away from the currently saturated pixel or group of pixels so that they do not saturate as quickly due to the proximity to already saturated pixels.

A SMSLS system of method with such an additional feature can increase EDR up to 50-fold, and possibly more, with no cross-talk between pixels from adjacent fibers. This represents an enormous increase in the SMSLS dynamic range of detection. In a poorly designed fiber optic coupling to CCD, intensity from the Gaussian intensity distribution of one fiber can 'bleed over' onto pixels belonging to an adjacent fiber.

There are many contexts in which EDR can be useful. In solutions containing polymers and colloids whose scattering increases in time, this can be of decisive value. Some examples include, but are not limited by:

i) A stimuli responsive polymer, such as Poly-n-isopropyl acrylamide (NIPAM) and its copolymers has a lower critical solution temperature (LCST) at which point the polymer chains collapse from random coils to globules, which begin to reversibly aggregate. When this phase transition at the LCST occurs the light scattering intensity increases dramatically, often by orders of magnitude. EDR will keep the light scattering measurements before and after the LCST on scale.

ii) Many therapeutic proteins have a tendency to aggregate, which has negative consequences for drugs composed of these, since aggregated proteins lose their therapeutic bioavailability and can even be antigenic. The U.S. Food and Drug Administration, the National Institutes of Standards and Technology, as well as scores of pharmaceutical/biotechnology companies are actively engaged in studying protein aggregation processes, and how they can be minimized or eliminated. Light scattering intensity can increase dramatically as aggregation proceeds and EDR will allow measurements of light scattering from extensive protein aggregation to remain on scale.

iii) There are many types of flocculants for water treatment in municipal systems, metallurgy, paper making, oil recovery, etc. Flocculation leads to large increases in light scattering and EDR will allow such processes to be measured, on scale, over wide ranges.

iv) A very wide range of polymer and colloids are inherently unstable in solution and will aggregate in time. EDR will allow such processes to be monitored over a much wider range than in the absence of EDR.

v) Many polymers and colloids are stable until a solution condition changes, such as pH, ionic strength, specific ions, chelating agents, surfactants, etc. EDR will allow exploration of destabilizing agents for such solutions.

Adaptation of the SMSLS Platform to Measure Other Properties Besides Total Scattered Intensity The SMSLS systems herein disclosed can be adapted to measure dynamic light scattering with for example, addition of single mode fibers and use of an autocorrelator for the intensity signal, and choice of homodyne or heterodyne mode of operation.

The SMSLS systems herein disclosed can be adapted to measure fluorescence for example, by putting notch or narrow band pass filters before or after fibers, if at 90° detection multiple vertical levels of filters could give extended fluorescence detection range. Generally lower wavelength lasers or very well steered broad band sources are used.

The SMSLS systems herein disclosed can be adapted to measure turbidity for example, by forward detection with a highly attenuated laser beam and possible logarithmic amplification).

The SMSLS systems herein disclosed can be adapted to measure optical activity, for example by rotation of polarization state with the use of natural polysaccharidic and proteinaceous natural products, which are virtually all optically active. Using polarizers and either mechanical or Kerr effect detection optical activity is measured.

The SMSLS systems herein disclosed can be adapted to measure optical activity UV absorbance utilizing a UV detector.

The SMSLS systems herein disclosed can be adapted to provide automatic continuous mixing.

The SMSLS systems and methods herein disclosed can be used for high throughput monitoring of the encapsulation and release of drugs by nano- and micro-carriers (e.g. dendrimers, cavitands, etc.) Additionally, the SMSLS systems and methods herein disclosed can be used for determining, real-time, high throughput dissolution, phase diagrams and microsolubility of protein and colloid solutions. Use of Specific Time Dependent Light Scattering Signatures to Interpret Kinetics of Aggregation or Degradation in Polymer Reactions, Including Enzymatic Reactions.

The SMSLS systems and methods herein disclosed can be used to measure specific time dependent light scattering characteristics of solutions. When polymers or colloids aggregate or degrade there can be a mathematically predictable time dependent light scattering signature associated with the process that reveal mechanistic and kinetic aspects of the process. Such processes include, but are not limited to, aggregation, enzymatic hydrolysis, enzymatic polymerization, synthetic polymerization, phase separation, phase transformations, etc.

User Protected Remote Access to Groups of Sampling Cells.

The SMSLS systems and methods herein disclosed can provide real-time access to data generated from one or more sampling cells in an array of sampling cells. Polymer or colloid characteristic data or light parameter data can be streamed to interested users of the system on a cell-by-cell basis to provide real-time polymer and colloid data simultaneously to a plurality of users. Each sample cell or group of sample cells can be user name and password protected to provide secure and remote access to data generated from one or more sampling cells.

An SMSLS user searchable database can also be created to provide remote offline and online user access to data generated from one or more user assigned sampling cells. Data generated from one or more sampling cells can be measured, collected and stored in a database that provides secure and remote access to polymer or colloid solution data generated from the SMSLS systems and methods herein disclosed.

Particulates that Form During Protein Aggregation

Particulates in therapeutic protein formulations can arise from a number of sources; highly aggregated protein, silicone oil and adventitious particles from syringes, 'dust' and processing equipment. Protein aggregates can reduce drug availability and, worse, provoke allergic and immune responses, while metal and oil particles may create heterogeneous particles possessing even greater immunogenicity as well as other adverse physiological consequences. [Rosenberg, A. S. *AAPS Journal*, 2006, 8, E501-E507; Schellekens, H. *Discov Med*, 2010, 9, 560-564.]

The U.S. Food and Drug Administration (FDA) has an interest in regulating these and the U.S. National Institute of Science and Technology (NIST) is seeking means of standardizing their characterization. Major efforts are underway to better characterize particulates in protein solutions. [Malloy, A. *Materials Today*, 2011, 14, 170-173; Filipe, V.; Hawe, A.; Jiskoot, W. *Pharma Res*, 2010, 27, 796-810; Barnard, J. G.; Singh, S.; Randolph, T. W.; Carpenter, J. F. *J Pharm Sci*, 2011, 100, 492-503; Huang, C. T.; Sharma, D.; Oma, P.; Krishnamurthy, R. *J Pharm Sci*, 2009, 98, 3058-3071.] The issue of "subvisible" particles and the need for more rigorous quantification, monitoring and control has received much attention in recent years. [Carpenter, J. F.; Randolph, T. W.; Jiskoot, W.; Crommelin, D. J. A.; Middaugh, C. R.; Winter, G.; Fan, Y.-X.; Kirshner, S.; Verthelyi, D.; Kozlowski, S.; Clouse, K. A.; Swann, P. G.; Rosenberg, A.; Cherney, B. *J. Pharm. Sci.* 2009, 98, 1201-1205.]

Historically, the control of aggregates and particles in biotechnology products has relied almost exclusively on SEC for soluble aggregate quantification and on light obscuration methods for particle counting. However, particles within the size range 0.1 µm to 10 µm have been largely overlooked, despite awareness that particles within this range are capable of provoking immunogenicity. The biotechnology industry is striving to identify new and improved methods capable of detecting particles within this range, as well as methodologies to more effectively probe their origins and how bioprocessing methods and stresses influence this. The potential connection between subvisible and submicron particles has also been noted and recent studies have begun to explore these interrelationships with a goal of better understanding product robustness and predicting stability. [Bai, S.; Murugesan, Y; Vlasic, M.; Karpes, L. B.; Brader, M. L. *J. Pharm. Sci.* 2013, 102, 347-351.] Emerging LS-based methods are likely to play an important role in providing more sensitive approaches to probing the earliest stages of protein aggregation and how the progression to submicron, subvisible and visible particle formation occurs. SMSLS will aid in the characterization of particulates via its ability to resolve individual large particles that cause light scattering spikes, LSS.

The term Heterogeneous Time Dependent Static Light Scattering (HTDSLS) was introduced by Schimanowski et al. in connection with their instrument that could resolve and count LSS from individual large particles and simultaneously measure the background scattering from a population of homogeneous scatterers. [Schimanowski, R.; Strelitzki, R.; Mullin, D. A.; Reed, W. F. *Macromolecules*, 1999, 32, 7055-7063.] The 'heterogeneous' in the acronym refers to the fact that the solution contains both particulates and a background population of much weaker scatterers. The authors of that work were able to determine particle number density in solutions while recovering the background scattering. A demonstration was made by growing *E. Coli* bacteria in a broth in which poly(vinylpyrrolidone) (PVP) was dissolved. HTDSL furnished the increase in time of the bacterial populationa and characterization of PVP $M_w$ and $R_g$.

One of the conditions for performing HTDSLS is that there be relative motion between the incident beam and the particles. This ensures that particles pass swiftly through the scattering volume, yielding well defined LSS. Schimanowski et al. provided this by using a light scattering flow cell.

There are many cases where a solution contains a background population of scatterers that scatter light uniformly at any given time and scattering angle, and a population of large scatterers, each large particle scattering many orders of magnitude more light than an individual background scattering particle. Such systems include, but are not limited to: i) Large protein aggregates in a solution containing a uniform background of proteins not in the form of large aggregates, ii) Solutions containing a uniform background of proteins not in aggregated form in which large non-protein scatterers exist, such as biological cells, bacteria, viruses, cell fragments, or oil nano- or microdroplets, metal, plastic, or glass particles, etc., iii) Solutions containing a uniform background of natural or synthetic polymers and a population of colloid particles, such as bacteria in a polysaccharide-based fermentation liquid, microgels in a solution of acrylamide based copolymers, etc.

A large particle means any particle that scatters sufficient light to produce a detectable light scattering spike. The sensitivity of the light scattering system hence sets the lower limit on what is considered a large particle. In some embodiments, a large particle may be 0.1 microns, or even smaller. In other embodiments, a large particle may be a single gas atom capable of being detected as a light scattering spike if dilute enough and sufficiently sensitive detection means are available. In yet another embodiment, a large particle may be an individual particle which is contrasted to a background scattering particle. The term 'Large particle' will be used as a convention in what follows, to indicate a particle large enough to produce a detectable scattering spike against a uniform background. In general, large particles capable of producing individually measurable LSS will range from about 0.1 microns up to hundreds of microns, that is up to particles so large as to be visible to the naked eye. It is also noted that size is not the sole determining property controlling light scattering intensity. A solid particle of 0.05 micron radius can be expected to scatter roughly 1,000 times more than a random coil molecule of 0.05 micron root mean square radius of gyration, a molar mass of $2.4 \times 10^6$ g/mole and the same index of refraction as the solid particle.

An important aspect of the types of samples the current disclosed technology will be used for concerns their stability. Namely, there are many solutions containing synthetic or biological macromolecules, and/or colloids, that are not in equilibrium and hence evolve in time. The evolution may manifest itself in many ways. For example, the particles may aggregate, the particles may aggregate and precipitate, the particles may form microgels or microcrystals which may then be stable for a long period of time or may eventually precipitate, the particles may degrade into smaller fragments or molecules such as the chemical or enzymatic degradation of a macromolecule, the particles may phase separate, the particles may undergo a chemical reaction driven by deliberate agents (e.g. a polymerization reaction) or ambient agents (oxygen, temperature, humidity), the particles may dissolve, etc. When these instabilities occur on a relevant time scale then it is often advantageous to be able to measure the kinetics of such processes, and how the macromolecular, colloidal, and particle aspects of the solution change.

Solutions that do not change over relevant periods of time are considered 'stable' or 'quasi-stable'. 'Relevant periods of time' mean such periods over which it is important that a solution's characteristics do not change. A relevant period of time may be that the shelf-life of a drug may be two years.

As long as the drug on the shelf is stable or substantially stable over two years then this is the relevant time period. Another example of a relevant period of time is illustrated where a measurement is made on a micellar system containing impurities. The system is stable for a few days only and an experiment takes less than an hour. In this illustration, the system is stable for the relevant time period of the experiment. Another example of a relevant period of time is illustrated using the concept of permanent magnetization of a ferromagnetic material (e.g. iron). The magnetization will eventually be lost due to thermal effects (Néel relaxation). However, it can take millions of years for the ferromagnetic material to lose magnetization. A human user of the magnet declares the magnetization permanent, because it remains magnetized throughout a human lifetime which is the relevant period of time in this case.

Heterogeneous time dependent static light scattering (HTDSLS) is a means of simultaneously detecting background scatterers and large particles. This method utilizes liquid samples that flow through a scattering cell to produce a measurable light scattering spike (LSS) each time a large particle passes through the scattering volume of the sample cell. The scattering volume refers to that part of the sample illuminated by the incident light beam that is detected by the system's detection optics. In some embodiments, the scattering volume is on the order of fractions of a nanoliter to hundreds of nanoliters for typical light scattering.

In some embodiments, a batch mode SMSLS with stirring capabilities may achieve the relative motion between the sample solution and the incident light beam used in the scattering experiment and hence HTDSLS performance. In some embodiments, the SMSLS system may utilize controlled stirring RPM's. Stirring, whether the RPMs are controlled or not, will ensure that large particles are forced to pass through the laser beam in a well-defined amount of time, producing light scattering peaks. Left unstirred, particles will diffuse through the light scattering volume in a random way and may produce extended peaks of undefinable width as a particles meander in and out of the scattering volume.

Figure 8:
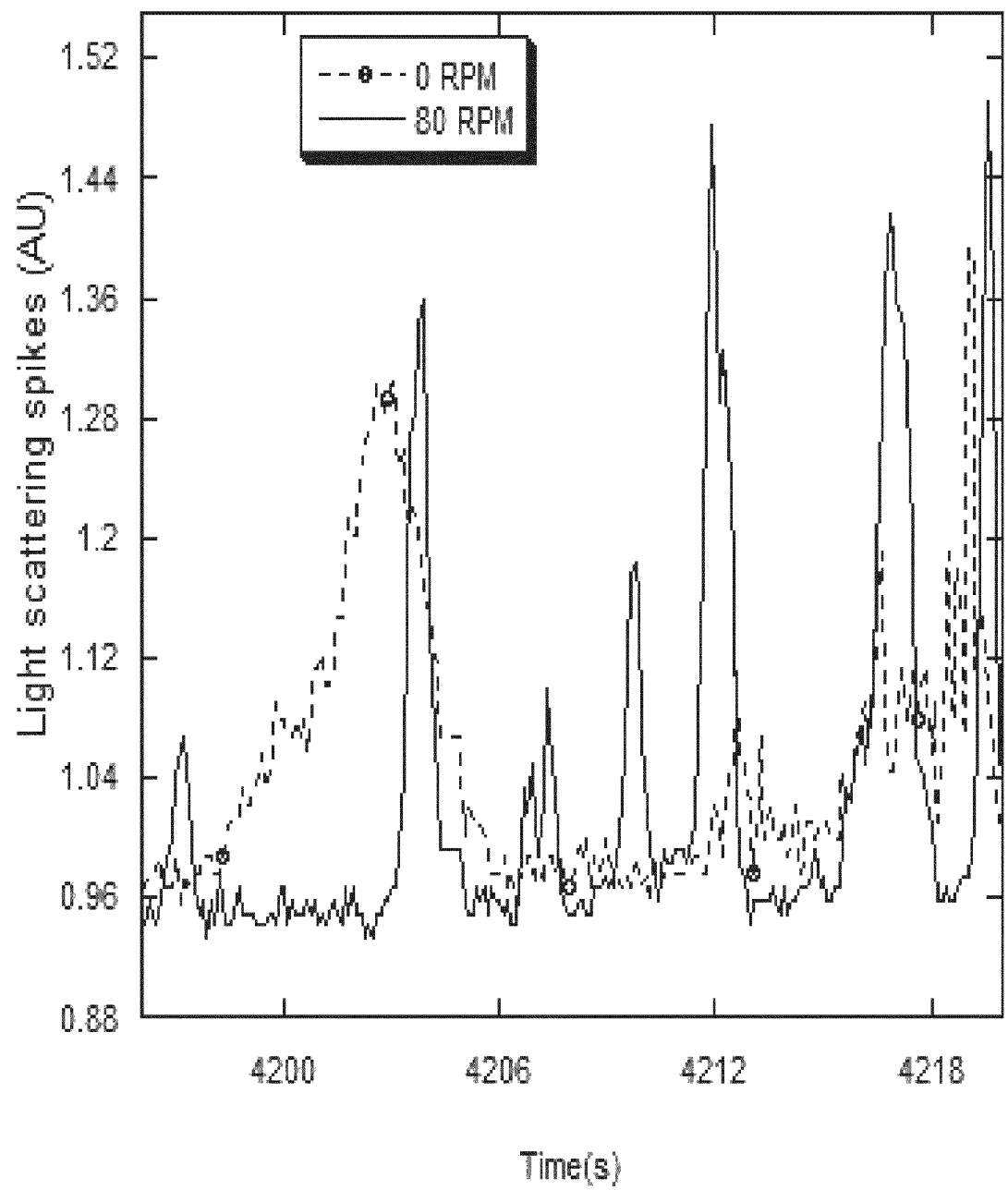
FIG. 8 illustrates a plot of light scattering peaks for a dilute solution of 2 micron (m) latex spheres in water under diffusion-control (i.e. 0 RPM) and stirred at 80 RPM.

FIG. 8 illustrates this point where thirty second swaths of data are shown for a dilute solution of 2 micron (µm) latex spheres in water under diffusion-control (i.e. 0 RPM) and stirred at 80 RPM. As depicted in FIG. 8, the diffusion-controlled scattering spikes are of broad and random width and occur at irregular intervals. The 80 RPM spikes have narrower and more uniform widths and occur more frequently. The difference in heights of the various peaks is related to which portion of the laser beam's intensity profile in the scattering volume that the particle traverses.

In the SMSLS system, the stirring feature can be used to provide the relative motion. FIG. 8 shows light scattering peaks from 2 µm latex spheres in water, collected from the SMSLS system for the case where i) there is no relative motion and the LSS are diffusion controlled and ii) when 80 RPM stirring was used. Sampling was at 10 Hz. The diffusion controlled peaks are of irregular shape and duration, whereas the LSS at 80 RPM are well defined, have narrower and more tightly controlled widths, and occur more frequently. Because the beam intensity over the scattering volume is not uniform even monodisperse particles such as these produce a distribution of LSS peak heights. Taken over a long enough sampling period the integral of the LS intensity over time is the same for both cases i) and ii), as expected.

Importantly, when the area under the diffusion-controlled LSS spikes are integrated over a long time the area is the same as when the 80 RPM spikes are integrated over the same period. On average, diffusion-controlled particles spend the same amount of time in the beam as those that are stirred. This is the expected statistical result. Its practical value is that controlled stirring can be used to control the average width and average frequency of the individual spikes, turning the stirring capability into a powerful tool for monitoring particulates in protein solutions, since particles can literally be observed one by one as they pass through the scattering volume and many thousands of particles can be detected in the course of an experiment, producing a large statistical database for analysis. For example, by no means limiting, is that a particle could be counted every second, so that in the course of a one hour experiment over three thousand spikes are available for analysis. Characterization of particulates in protein solutions is a major issue across the biotechnology and pharmaceutical sectors. The U.S. NIST (National Institute of Standards and Technology) is attempting to standardize particle measurement, and attempting to set regulations on particulate content in therapeutic protein formulations is a goal that FDA (Food and Drug Administration) is striving towards. The current disclosed technology provides a new tool in this area and other areas including the characterization of particulates from synthetic or natural sources, where particle size might be an indicator of quality or other desired parameters. Some examples include nanoparticles, synthetic polymers, biopolymers, carbon nanotubes, and other natural or synthetic materials.

Another application of potential importance concerns particles with tensorial polarizability $\overline{\alpha}$ such that the electric dipole induced by the incident beam $\vec{p}$ is not aligned with the incident beam electric field $\vec{E}_0$. The incident beam is expressed by:

$$\vec{p} = \overline{\alpha} \cdot \vec{E}_0$$

In this case, scattered light will have a detectable depolarized component that particles of scalar polarizability $\alpha$ do not have. Such particles normally have anisotropic morphologies such as rods, ellipsoids, etc. Hence, it is possible to measure LSS from anisotropic particles either alone or that co-exist with isotropic particles. In this latter case it will be possible to separate the number density and MWD of the anisotropic particles from the particles of scalar polarizability. Most polymers and colloids in the sub-micron range have scalar polarizability and hence do not produce depolarized signals. In order to achieve the best detection the incident light on the scattering sample will be linearly polarized. It may also be elliptically polarized (of which circular and linear polarizations are special cases). Unpolarized incident light is the least favorable means for measuring depolarization.

For example, anisotropic biological particles, such as rod-like bacteria or viruses can exist in a mixture of other particles, such as isotropic cells, cell fragments, blood plasma, etc. Using the depolarized LSS, their number density and characteristics could be determined using the various LSS MWD analysis methods outlined herein. How such populations might change in time, increasing or decreasing, including in response to nutrients or drugs, can also be monitored.

In other instances, anisotropic proteins, such as the fibrillar amyloid aggregate type found in Alzheimer and related diseases could be detected amidst other particles and their number density and MWD characteristics obtained. It is also possible to monitor the increase or decrease of these due to natural or human-applied causes. For example, a drug that dissociates amyloid protein aggregates would lead to a decrease in number density of the aggregates and decrease in the MWD and its averages.

Carbon nanotubes are generally anisotropic and can produce depolarized scattering. When co-existing with other particles that are not anisotropic, e.g. in composites and solutions made therefrom, it would be possible to use the depolarized LSS to characterize the nanotube population. Nanotubes also have a strong propensity to aggregate. The aggregates will normally have different depolarization properties, so that the depolarized LSS method may be used as a tool to characterize dispersion and stability properties of nanotubes in solution. For example, nanotube aggregates may lose or greatly reduce their tensorial polarizability leading to a mixture of anisotropic (unaggregated nanotubes) and isotropic or quasi-isotropic particles.

Particles much larger than the wavelength of incident light can depolarize light regardless of their morphology. An example of this is particles whose size is several microns or greater. Hence, depolarized LSS spikes can be used to separate out scattering from very large particles from other, smaller particles that produce LSS, but are not large enough to produce significant depolarized LSS. Such particles can form in many types of processes, such as production of synthetic polymers in homogeneous and inhomogeneous phase, synthetic rubber and water purifying chemicals, processing of natural products such as polysaccharides, R&D and production of therapeutic proteins, and many more cases.

Figure 9:
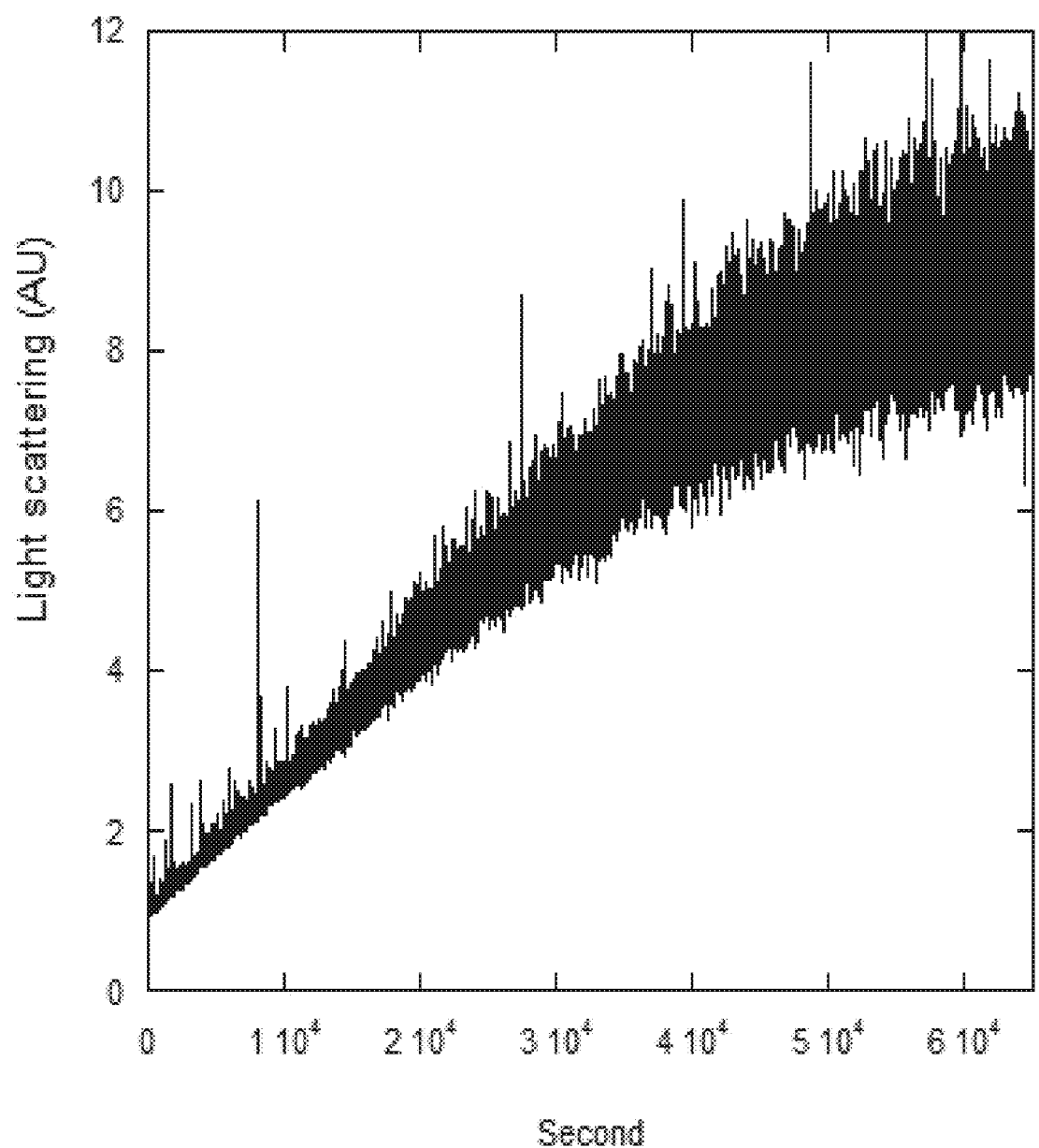
FIG. 9 illustrates a plot of particulates forming for a protein when stirred with no air/liquid interface at 100 RPM at 0.010 g/cm$^3$.

The increasing width of the light scattering data in FIG. 9 shows particulates forming for a protein when stirred with no air/liquid interface at 100 RPM at 0.010 g/cm$^3$. FIG. 9 shows how the width of the scattering can increase in time as a protein aggregates. The broadening appears as a noisier signal. In fact, the increase in the width and apparent noise is due to the onset and evolution of a particulate population in the protein solution. The increasing width of the light scattering data in FIG. 9 shows particulates forming for a protein when stirred with no air/liquid interface at 100 RPM at 0.010 g/cm$^3$.

Figure 10:
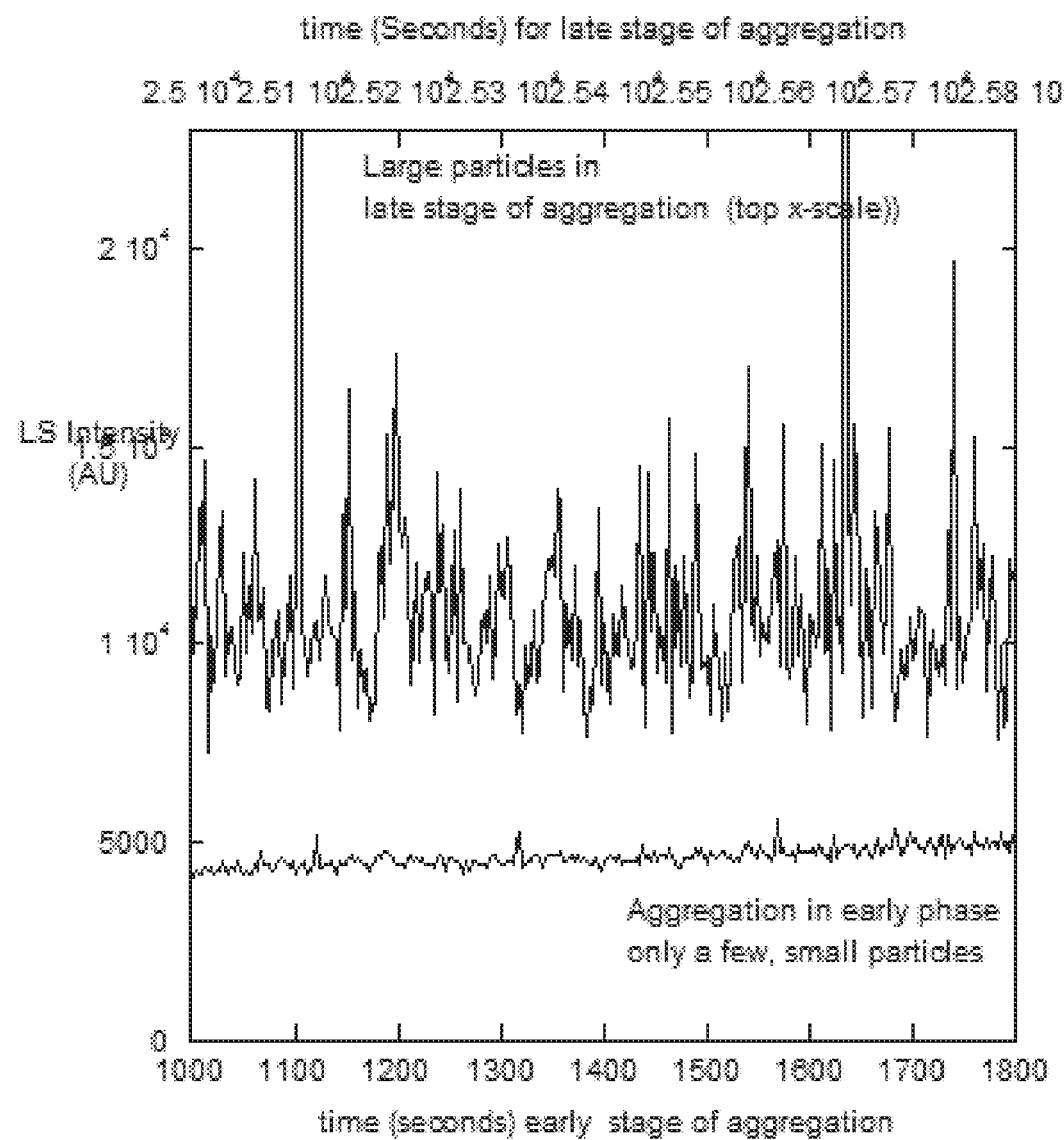
FIG. 10 illustrates a plot of two 500 s swaths of the data from the strongest scattering sample of FIG. 9.

To illustrate this, FIG. 10 shows two 500 s swaths of the data from the strongest scattering sample of FIG. 9. As depicted by the lower x-axis of FIG. 10, it is seen that early in the aggregation process there are very few spikes. In the early swath there are few particulates, and these are small, as seen by the low amplitudes of the LSS. Later in the aggregation process, for a 500 s swath starting at 25,500 s, the particulate population has a higher number density and the particles are much larger. This is attributed to the fact that protein aggregates at this stage are still soluble and sub-micron in size. As depicted by the upper x-axis of FIG. 10, numerous spikes of varying width and height are seen after 25,000 seconds, clearly showing the presence of large, >1 micron, size particles.

Work is currently in progress to use the LSS spectra to obtain particle density and how it changes in time, and a measure of the molar weight distribution for the particles.

Figure 11:
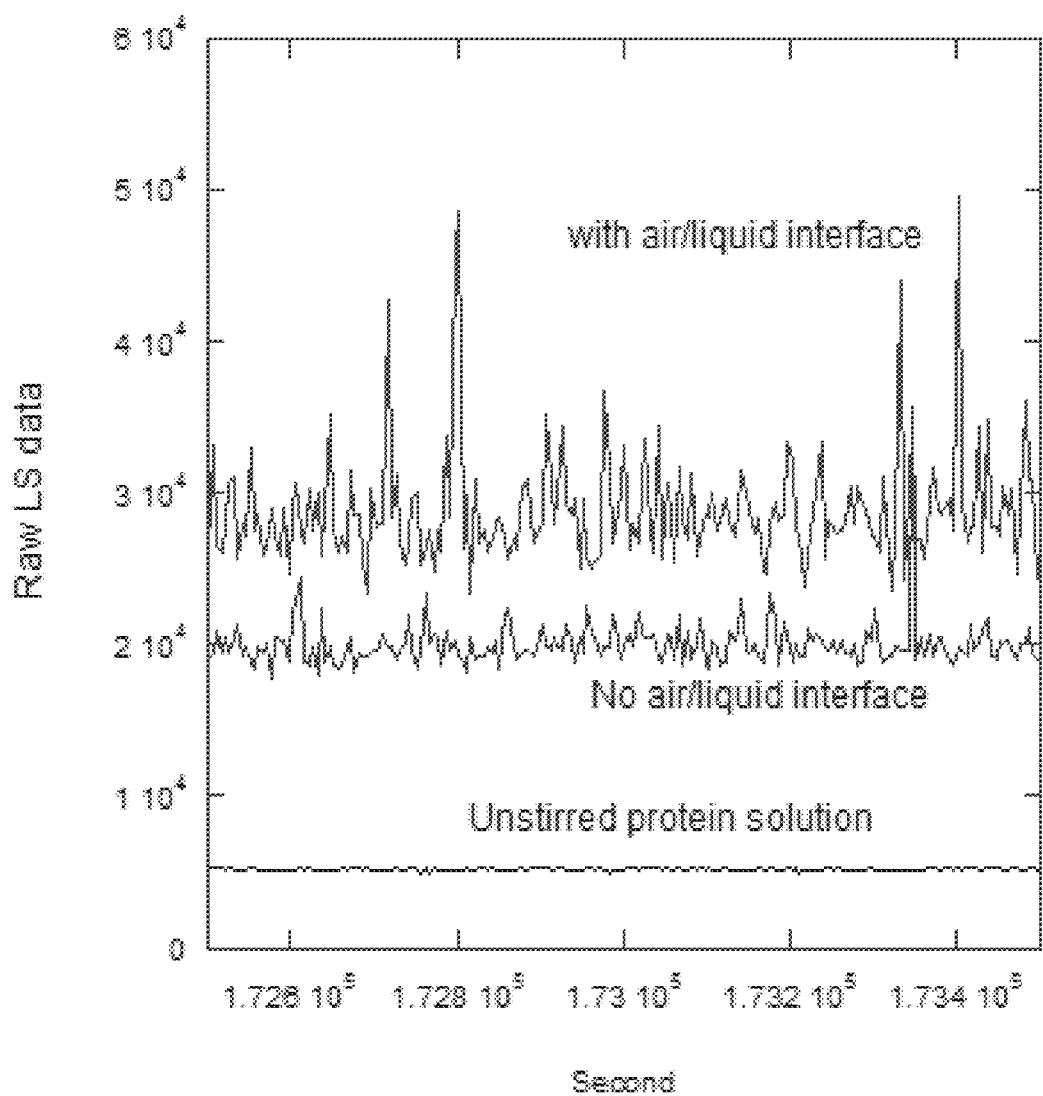
FIG. 11 illustrates a plot of protein samples with no stirring stress, stirred at 100 RPM with an air/liquid interface and stirred at 100 RPM with no air/liquid interface.

FIG. 11 shows protein samples with no stirring stress, stirred at 100 RPM with an air/liquid interface and stirred at 100 RPM with no air/liquid interface. FIG. 11 shows the difference in particulate content for these three samples taken from a 500 s data swath after 2.5 days. The sample with the air/liquid interface has larger particles and a higher concentration of particles compared to the sample with no air/water interface. The unstirred control sample is seen at the bottom. No aggregation or particulation occurred in the unstirred sample over the three day experiment at 35° C.

Many types of analyses can be carried out on the SMSLS spike spectra and uniform background scattering data. These analyses include but are not limited to:
a) obtaining the number density of large particulates and how these change in time, if at all. The number density may be a relative or absolute number.
b) obtaining the definition of large particle that produces LSS
c) calculating molar mass (M) of large particles
d) cross-checking M by use of calibrated standards. For example NIST latex spheres.
e) correct for angular effects under certain simple assumptions
f) calculating size, such as Radius (R), or large particles
g) finding averages of M when large particles are polydisperse
h) finding averages of R when large particles polydisperse
i) computing the Molar Weight Distribution (MWD) of polydisperse large particles
j) computing the Particle Size Distribution (PSD) of polydisperse large particles
k) computing the transfer of mass, or, equivalently, concentration, from uniform background scattering native proteins and aggregates into large particles, and vice versa in the case where large particles decompose into uniform background scatterers.
l) determining onset of precipitation and precipitation rates
m) determining the incident laser intensity distribution in the scattering volume $V_s$
n) determining $V_s$ using LSS counting and analysis Number density is in terms of particles/volume e.g. particles/cm$^3$. Determining particle number density should be understood by one skilled in the art and is applicable to data gathered by the disclosed technology. The analysis used to determine particle number density is dependent on clear window time, which is the average time in which there are no particles in the scattering volume, which then defines the average time between LSS in the scattering volume. Further, the analysis can involve the use of the binomial distribution to compute the probability of one or more particles occupying the scattering volume at any instant to determine the probability of a single particle detection to vary as exp(−n $V_s$) where n is the particle number density and $V_s$ is the scattering volume.

In the case where $V_s$ is so small that there are multiple large particles in $V_s$ at the same time, this product can be reduced by reducing either n or $V_s$ or both. In the first case, the sample may simply be diluted. In the second, a modification to the SMSLS system is made. It is possible to: i) use an optical detection fiber of narrower diameter and/or smaller numerical aperture ii) focus the beam to have a tight beam waist, and iii) ensure that the fiber is operating in pinhole mode. If there are more than one particle on average in $V_s$ the method begins to breakdown as particles are then no longer individually detected.

The current disclosed technology includes data analyses of a type not previously disclosed, published, or known by one of ordinary skill in the art. Namely, a measure of the large particle Molar Weight Distribution (MWD) can be computed from the methods of this disclosed technology. First, such measurements should be made at the lowest possible detection angle of a given SMSLS unit, preferably less than 30°, and more preferably less than 10°, and even more preferably by extrapolation to 0°, but even at 90° useful approximations to the MWD can be measured.

The problem is not as straightforward as it may seem because, usually, the laser incident intensity throughout $V_s$ is not uniform, which means the analysis becomes doubly statistical. For example, there will be a LSS amplitude spectrum from even monodisperse particles which must be accounted for. Secondly, MWD adds the second layer of statistics. In the most ideal case, the beam over $V_s$ would be treated as a short cylinder with an intensity in the TEM 00 mode that dies off as a Gaussian function of distance from the center of the beam. In reality, axial asymmetry from lasers, especially diode lasers, effects of optics in the beam paths, admixtures of higher normal modes, etc. can lead to other than a Gaussian beam profile and a non-cylindrical volume shape. Furthermore, the particles in angular motion due to a stir bar do not necessarily cross the laser beam at right angles.

Figure 12:
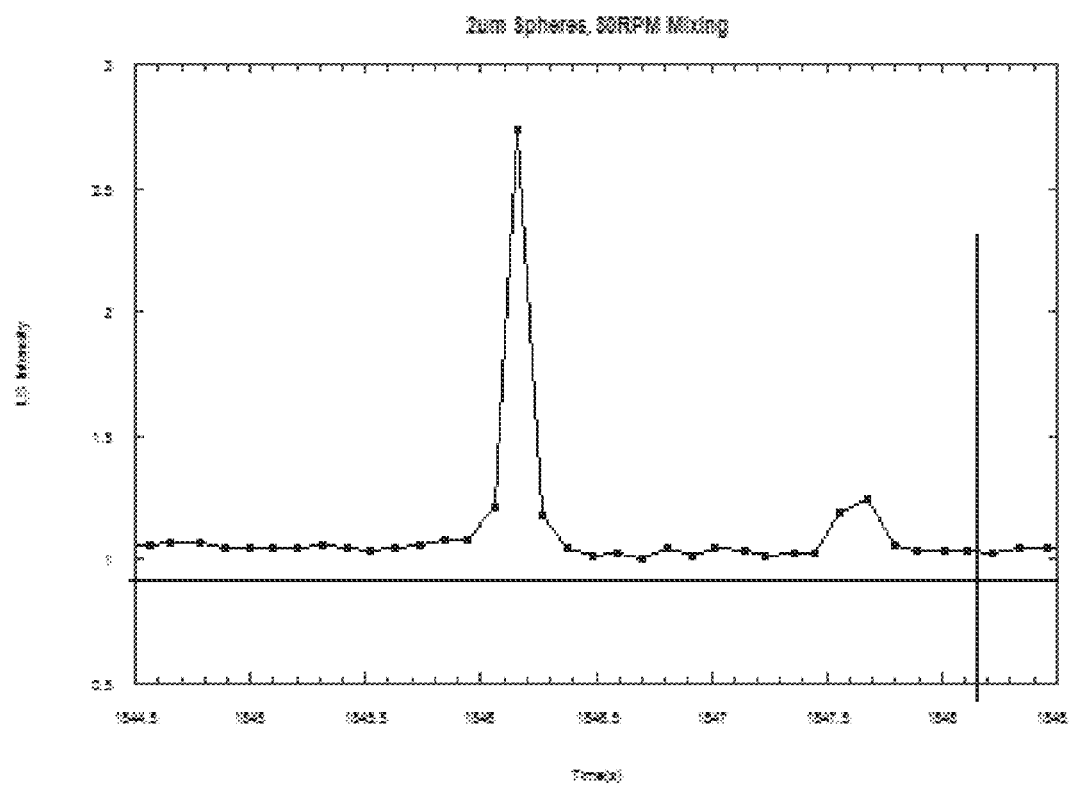
FIG. 12 illustrates a plot of a zoom-in on a single LSS spike.

It is important to define the requirements for resolving LSS. FIG. 12 shows a zoom-in on a single spike from data above. The sampling rate is approximately 10 Hz. While the main spike is clearly seen the sampling rate is not high enough to provide adequate time resolution to see the full shape of the spike. In FIG. 12, the LSS, with three sampling points (one on the rise, one at the maximum, and the third on the fall) can be declared to be measured, or detected, but not 'time-resolved'. Measurement of the spike is useful in itself as it will give knowledge of particle number concentrations, and the peak can be used as an estimate of the true peak height; as it is, the true height may be somewhat higher than the highest point on the spike, and occur a bit before or after the measured maximum. A fully time-resolved spike would have a sufficient number of data sampling points that both the width and height of the spike could be determined to an acceptable level of precision. A minimum number of sampling points may be five—two to mark the onset of the spike, one each on the rise and fall of the spike, and a point at the maximum. With this, interpolations for better estimating the peak height can be made. Naturally, the faster the sampling and the higher number of sampling points during an LSS the higher the precision will be for determining the maximum and the shape. The time-resolved shape will allow the width of the LSS to be computed. The shape may also yield further details of the light beam intensity distribution in the scattering volume and the trajectory through it of the particle causing the LSS. It should be noted that sampling too slow will not only fail to time-resolve the LSS but may lead to missed LSS, thereby leading to erroneous characterization of particle number densities. Such undersampling would also lead to errors in MWD and size distribution analyses.

The sampling rate needed for time-resolved capture of LSS depends on the amount of time the particle spends in the scattering volume. This, in turn, depends on the stirring rate, geometry and dimension of the scattering volume, the stirring mechanism, and the trajectories produced in any given cell by the stirring mechanism and RPMs. For the particular example in FIG. 12, the minimum sampling rate for capture of five points would be approximately 20 Hz, instead of the 10 Hz used, which would increase the number of sampling points on the LSS to about six.

Figure 13:
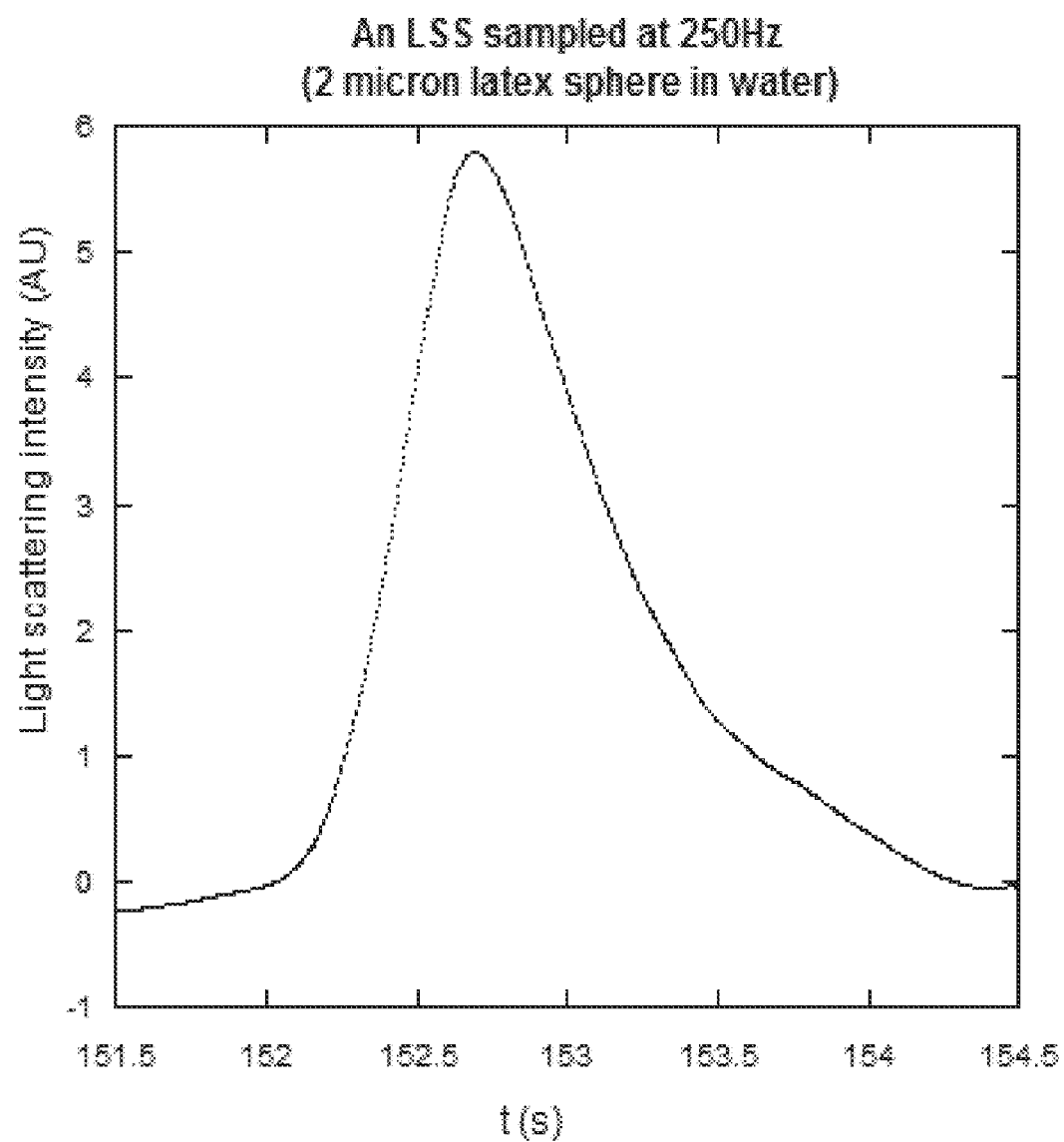
FIG. 13 illustrates a plot of an LSS sampled at 250 Hz.

FIG. 13 shows an example of an LSS sampled at 250 Hz. As seen, there are over 300 individual sampling points comprising the LSS, yielding more than adequate resolution of the LSS In general, sampling rates are expected to run from the order of one Hertz up to several thousand Hertz, with sampling rates between 10 and 1,000 being most common. It is easy to envision specific embodiments where other ranges might be used. For very low stir rates less than 10 Hz sampling may be adequate. By contrast, for very high stir rates sampling rates in excess of 1,000 Hz may be required.

Under normal operating conditions for this disclosed technology the flow produced by the relative motion between the liquid sample and the scattering volume should be non-turbulent.

A means of determining the beam intensity profile, independent of the details of the spatial intensity of the beam and the trajectories of particles passing through it, is as follows: Uniform scatterers, such as 2 μm spheres are used at very dilute levels. The stirring must be such as to produce non-turbulent, rotational flow. The particles are stirred and pass through the scattering volume on trajectories that will be, on average, the same for all dilute particle solutions. A histogram of LSS heights from the detector will then provide an intensity distribution of the beam in terms of $W(I_R,M)$. $W(I_R,M)dI_R$ is the probability that a particle, of a population of identical particles of molar mass M, will produce a spike of magnitude $I_R$ to $I_R+dI_R$. The distribution is normalized as follows:

$$\int_0^\infty W(I_R,M)dI_R=1$$

The shape of this distribution is a universal curve for the system that depends only on the incident beam intensity distribution within the scattering volume $W(I_0)$. Here, $W(I_0) dI_0$ is the probability that the incident intensity in a random point in the scattering volume lies between $I_0$ and $I_0+dI_0$. Monodisperse particles of any size will give the same shape of $W(I_R(M))$, related to $W(I_0)$.

$$W(I_R,M)=W(I_0/\sigma N_2 M^2)$$

The Rayleigh scattering ratio $I_R$ (1/cm) for dilute scattering particles of number concentration N is the following:

$$I_R=k^4\alpha^2 N \sin^2 \phi$$

where $\phi$ is the altitude angle measured from the direction of the vertically polarized electric field in the incident light. $\phi=90°$, which gives the maximum scattering and is termed the scattering plane, is the plane normally used by most light scattering instruments. $\alpha$ is the polarizability of a single particle.

The scattered light intensity I, from a single particle at distance r from a Rayleigh scatterer of polarizability $\alpha$ is proportional to the incident intensity of the laser field at that point $I_0$, and for a Rayleigh scatterer is given by the following:

$$I = \frac{8\pi^4 \alpha^2 \sin^2 \phi}{\lambda^4 r^2} I_0$$

In general, $\alpha$ is proportional to the molar mass of the particle.

Under the assumption that large particles of all sizes are swept through the beam in the same manner, and the assumption of very low scattering angle, the shape of $W(I_R(M))$ will be the same for monodisperse large particles of any mass.

For any particle of given mass M the intensity weighted LSS peak height will be proportional to $M^2$ as follows:

$$<I_R>=\int_0^\infty I_R W(I_R,M)dI_R \propto M^2$$

After $W(I_R)$ has been determined, it should be the same for a given RPM in a given cell geometry. A polydisperse population of non-interacting large scatterers has a distribution of masses, N(M), where N(M) dM is the number density of particles with molar masses between M and M+dM. We define $s(I_R)dI_R$ to be the number of spikes in an LSS spectrum between $I_R$ and $I_R+dI_R$. The total number of spikes in an LSS spectrum, $S_t$, will be the superposition of $W(I_R(M))$ resulting from each part of the molar mass distribution $N(M)$, according to the following:

$$S_t = \beta \int_0^\infty \int_0^\infty N(M) W(I_R, M) dM dI_R$$

where $\beta$ is a proportionality factor given by the $S_t$ and the total number of particles $N_{total}$ as follows:

$$\beta = \frac{S_t}{\int N(M) dM} = \frac{S_t}{N_{total}}$$

This means that the sought after $N(M)$ is directly related to the number of LSS due to particles in the interval M to M+dM, $S(M)dM$ by $S(M)=\beta N(M)$. Since $\beta$ is just a proportionality factor, $N(M)$ can be found from the integral above, which is equivalent to the following:

$$S_t = \int_0^\infty \int_0^\infty S(M) W(I_R, M) dM dI_R$$

In order to gain information about the large particle population, $N(M)$ is to be extracted from the integral. The disclosed technology allows any number of ways for this extraction to take place, including, but not limited to: i) inversion of the integral by Fourier transform or other transform methods, ii) histogram methods such that the integral is taken as a sum over molar weight intervals $\Delta M$, iii) average methods where moments of the distribution are computed.

For example, the $W(I_R, M)$ and the experimental LSS amplitude spectrum may be used as follows to determine the product of weight average and number average masses, $M_w$ and $M_n$, respectively:

$$\frac{\int_0^\infty \int_0^\infty I_R N(M) W(I_R, M) dM dI_R}{\int_0^\infty \int_0^\infty N(M) W(I_R, M) dM dI_R} \propto N_2 M_w M_n$$

The statistical burden involved in such analyses may be reduced by making the incident light intensity in the scattering volume more uniform. If a uniform or near uniform intensity can be achieved then the following equation applies:

$$W(I_0) = \delta(I_0 - I_{0,u})$$

The delta function is the idealized form for expressing the uniformity of incident light intensity in $V_s$. In reality, the width of $W(I_0)$ could be greatly decreased so that it is essentially uniform throughout $V_s$.

If uniform or near-uniform incident intensity in $V_s$ is achieved, the double integrals above collapse to single integrals over M, which is the relevant integral for particle characterization. The integral over $I_R$ in the double integrals is a 'statistical annoyance' caused by beam non-uniformity.

There is an entire scientific and technical field that deals with shaping intensity profiles in laser beams. A popular shape to produce is the flat-top distribution i.e. a uniform intensity across the beam diameter. For example, a product line for producing uniform laser beams from initially Gaussian beams should be appreciated by one skilled in the art. There are a number of ways to make beams uniform, involving anamorphic optics, materials with graded index of refraction, and others. A particularly popular means of producing a homogenized 'top-hat' intensity profile in a laser beam is the use of microlens arrays, which can mix the intensities together of the various cross-sectional intensities of the beam incident on the microlens array. Often, the mixed intensity output of such a microlens is re-grouped by a second microlens array and can then be focused or collimated by additional individual lenses or other optical components.

Estimate of Particle Mass and Size for a Uniform Beam of Incident Intensity $I_0$ To understand some of the principles behind molar mass measurements from LSS spectra, the intensity of scattered light L from a dilute collection of Rayleigh scatterers of number density N (particles/cm$^3$) is given, in CGS unit, as mentioned above, by the following equation:

$$I_s = \frac{k^4 \alpha^2 \sin^2 \phi N}{r^2} I_0$$

Rayleigh scatterers' have a characteristic side D, such that $D \ll \lambda$, where $\lambda$ is the wavelength of the incident light. Such particles scatter isotropically in the scattering plane, $\phi = 90°$ for vertically polarized incident light.

Where $I_o$ is the intensity of vertically polarized incident light, a is the polarizability of the particle, or the difference in particle polarizability and solvent polarizability if the particles are in a solvent, such as proteins in aqueous solution, r is the distance from the scatterer to the detector, $\phi$ is the altitude angle measured with respect to the vertically polarized E-field of the incident light, and k is the wave-number, $k = 2\pi/\lambda$.

Consider two species of particles in the same solution, type 1 which has number density $N_1$ and molar mass $M_1$ and type 2 which has number density $N_2$ and molar mass $M_2$. The particles are again assumed dilute enough that interactions are negligible. The ratio of scattered light is then defined with the following equation:

$$\frac{I_{s,2}}{I_{s,1}} = \frac{\alpha_2^2 N_2}{\alpha_1^2 N_1}$$

This equation provides a means of making various types of analyses. For example, if both particles are of the same material, (e.g., native proteins and protein aggregates), then the specific polarizabilities will be the same, to a high approximation, and proportional to the respective molar masses so that, and in this case the following equation would apply:

$$\frac{I_{s,2}}{I_{s,1}} = \frac{M_2^2 N_2}{M_1^2 N_1}$$

Consider the case where type 1 is a native protein and type 2 is an aggregate. Let $v_1$ and $v_2$ be the number of particles in the scattering volume $V_s$ of type 1 and 2, respectively as expressed below:

$$v_1 = N_1 V_s \text{ and } v_2 = N_2 V_s$$

Further consider that to produce a single light scattering spike from the scattering volume $v_2 = 1$. $M_2$ can then be found by the following equation:

$$M_2 = \left(\frac{I_{s,2}}{I_{s,1}} v_1\right)^{1/2} M_1$$

$v_1$ is more conveniently expressed in terms of concentration $c_1$ (g/cm$^3$) by the following equation:

$$v_1 = \frac{c_1 N_A V_s}{M_1}$$

So that $M_2$ is expressed as follows:

$$M_2 = \left(M_1 c_1 N_A V_s \frac{I_{s,2}}{I_{s,1}}\right)^{1/2}$$

This allows computation of the minimum $M_2$ that will be detectable via a LSS and can hence be declared a large particle. This will be determined strictly by the stability of the light scattering system, so that there is no fundamental limit except as imposed by the various noise sources, including unavoidable thermal and quantum mechanical noise. There are means of improving signal to noise ratios, such as cooling semiconductor-based detectors, such as charge coupled devices (CCD).

For illustration suppose that an LSS at 1% of the uniform background scattering in a $10^{-3}$ g/cm$^3$ solution of an $M_1=10^5$ g/mole protein in a scattering volume of $V_s=10$ nL=$10^{-5}$ cm$^3$ $M_2=2.45\times 10^9$ g/mole is detectable; i.e. $I_{s,2}/I_{s,1}=0.01$. This is the minimum mass particle that would be considered a 'large particle' capable of producing an LSS via one particle in $V_s$.

Further, consider the case where the amplitude of the LSS is equal to the uniform background scattering from type 1; i.e. $I_{s,2}/I_{s,11}=1$, with all the other parameters the same. Then $M_2=2.45\times 10^{10}$ g/mole.

In terms of radius $R_2$ for spheroidal large particles of mass density $\rho_2$, $M^2$ can be expressed as follows:

$$M_2 = \frac{4\pi}{3} \rho_2 R_2^3$$

Or $R_2$ can be expressed as follows:

$$R_2 = \left(\frac{3}{4\pi\rho_2}\right)^{1/3} \left(M_1 c_1 N_A V_s \frac{I_{s,2}}{I_{s,1}}\right)^{3/2}$$

Using the above example for $I_{s,2}/I_{s,1}=0.01$ and $M_2=2.45\times 10^9$ g/mole, and taking $\rho_2=1$ g/cm$^3$ yields $R_2=10^{-5}$ cm=0.1 μm For the other example above, $I_{s,2}/I_{s,1}=1$ and $M_2=2.45\times 10^{10}$ g/mole, and again taking $\rho_2=1$ g/cm$^3$ yields the following equation:

$R_2=2.15\times 10^{-5}$ cm=0.215 μm

Importantly, these examples, especially the latter for which $I_{s,2}/I_{s,1}=1$ is easily achievable even in the most modest of SMSLS system, show that dense scattering particles become detectable at less than 1 micron. This gives an excellent low-end bracket in terms of a 'large particle' that can produce LSS.

Particle Size Limits on the Rayleigh Approximation

The upper end of the bracket is limited mainly by the lowest attainable angle. It is worth investigating up to what size the Rayleigh-Debye approximation continues to hold, before being required to invoke Mie theory for large particle analysis. The Rayleigh-Debye criterion is that the optical path length difference between light going through the characteristic dimension D of a scattering particle of index of refraction $n_p$ and light going through the solvent of index $n_s$ the same distance should be much less than the vacuum wavelength of the incident light, λ as expressed below:

$$\frac{D|n_p - n_s|}{n_s \lambda} \ll 1$$

For a typical protein in aqueous solution $n_p - n_s = 0.19$. For λ=635 nm, $n_s=1.33$, and the ratio:

$$\frac{D|n_p - n_s|}{n_s \lambda} = 0.1$$

This yields a characteristic dimension of D=4.5×10$^{-5}$ cm=0.45 μm. Taking the ratio as high as 0.4 means that the Rayleigh-Debye approximation may hold for particles up to about 2 μm. After this, diffraction or Mie analysis at lower angles would be advisable, although equivalent sizes could still be usefully obtained under the approximation, perhaps up to approximately 10 μm. Above this, under the Rayleigh-Debye approximation, results would be qualitative. The more water the large particles contain in their interior the better the approximation will be, and will hold to higher sizes.

Particle Size Limits Using the Zimm Equation Under the Rayleigh-Debye Approximation, and a Means of Correction without Multi-Angle Measurements Considering the large particles as spheres of uniform density (other distributions may also be used, such as Gaussian) means that the mean square radius of gyration $<S^2>=3R^2/5$. This can be used with the Zimm equation under the Rayleigh-Debye approximation for a single component expressed as follows:

$$\frac{Kc}{I(q, c)} = \frac{1}{MP(q)} + 2A_2 c$$

Where P(q) is the scattering form factor for the particle. For a particle with $$\frac{q^2 \langle S^2 \rangle_z}{3} \ll 1,$$

including a polydisperse system this becomes:

$$\frac{Kc}{I(q, c)} = \frac{1}{M_w}\left(1 + \frac{q^2 \langle S^2 \rangle_z}{3}\right) + 2\langle A_2 \rangle c$$

This directly permits determination of weight average molar mass $M_w$, double z-averaged second virial coefficient $<A_2>$ and the z-averaged mean square radius of gyration $\langle S^2 \rangle_z$. K is an optical constant, given for vertically polarized incident light as expressed by:

$$K = \frac{4\pi^2 n^2 (dn/dc)^2}{N_A \lambda^4}$$

Here, n is the solvent index of refraction, $\lambda$ is the vacuum wavelength of the incident light, dn/dc is the differential refractive index for the polymer in the chosen solvent, and q is the usual scattering wave-vector $q=(4\pi n_s/\lambda)\sin(\theta/2)$, where $\theta$ is the scattering angle. The $A_2$ term for the particulates is negligible in virtually all cases. For $n_s=1.33$ and $\lambda=6.35\times 10^{-5}$ cm $$\frac{q^2\langle S^2\rangle}{3} = \frac{q^2 R^2}{5} = 1.3\times 10^{10} R^2 \sin^2(\theta/2)$$

At $\theta=90°$ and $$\frac{q^2\langle S^2\rangle}{3} = 0.2$$

$R=5.4\times 10^{-6}$ cm=0.054 µm yields this error for $\theta=90°$. Hence, it will normally be necessary to go below $\theta=90°$. For example to detect a D=1 µm particle at the same 20% error level would require measurement at $\theta=10°$. Multi-angle SMSLS is one of the features that can be provided in the instrument.

An interesting correction can be made, however, even without using angles other than 90°. $M_2$ as described above, measured at a finite angle $\theta$ is denoted now as $M_{2,\theta}$, and this is related to the true value of the particle when extrapolated to $\theta=0$, $M_{2,0}$ as expressed by:

$$M_{2,\theta} = \frac{M_{2,0}}{\left[1 + \frac{q^2(\theta)}{3}\langle S^2(M_{2,0})\rangle\right]}$$

Any model can then be used for the morphology of particle 2; e.g. spheroid, random coil, rod, etc. In fact, one can relax the restriction on $$\frac{q^2\langle S^2\rangle_z}{3} \ll 1$$

and use a specific P(q) beyond this range in the computation (e.g. P(q) for a sphere).

To illustrate using the same supposition is used as earlier, that the particles are spheroidal one is working within $$\frac{q^2\langle S^2\rangle_z}{3} \ll 1$$

$$M_{2,\theta} = \frac{M_{2,0}}{\left[1 + \frac{q^2(\theta)}{3}\left(\frac{3M_{2,0}}{4\pi\rho}\right)^{2/3}\right]}$$

It is then easy to extract the corrected mass $M_{2,0}$ from this numerically.

Determination of Mass Transfer from Uniform Scatterers to Large Particles

Continuing in this case, if $N_2$ is determined by finding the average clear window time $\exp(-N_2 V_s)$, or other means, such as elaborated in Schimanowski et al, then it is possible to compute the transfer of the uniform background proteins and aggregates into the form of large particles, whose definition is given above.

Let $c_o$ be the initial concentration of material in solution, and for convenience assume that the material initially has no detectable large particles expressed as follows:

$C_o = c_1 + c_2$, at $t=0$ $C_o = C_1$

The concentration of large particles is given by the following equation:

$$c_2 = \frac{v_2 M_2}{N_A V_s} = \frac{N_2 M_2}{N_A}$$

Hence, once $M_2$ is determined, for example by the above method, then $c_2$ can be computed if $N_2$ is known. One method for computing $N_2$ is to use particles of known number concentration $N_{2,standard}$, such as NIST traceable latex spheres, and compute the average interval between LSS in a swath of LSS spectrum, or the average frequency. $N_{2,standard}$ can then be used to compute $N_2$ by comparing the average interval between LSS or average frequency of LSS.

It is also possible to find $N_2$ using clear window time (CWT), without recourse to standards, using the following equation:

$CWT = \exp(-N_2 V_s)$

CWT can be computed from LSS spectra from the average time $\langle\Delta t\rangle$ between LSS, of average width $\langle\tau\rangle$ as follows:

$$CWT = \frac{\sum_i \tau_i}{\sum_i \Delta t_i}$$

For example, say CWT is 0.1, $M_2=10^{10}$ g/mole and $V_s=10^{-5}$ cm$^3$, then $c_2=3.83\times 10^{-9}$ g/cm$^3$, which would be a tiny fraction of total material in a solution of $c_o=10^{-3}$ g/cm$^3$. $C_2$ could become more significant for larger $M_2$ and smaller CWT. Decreasing $N_2 V_s$ would be necessary to measure much higher $c_2$ in this example.

Non-Uniform Incident Intensity and Polydisperse Large Particles

Figure 14:
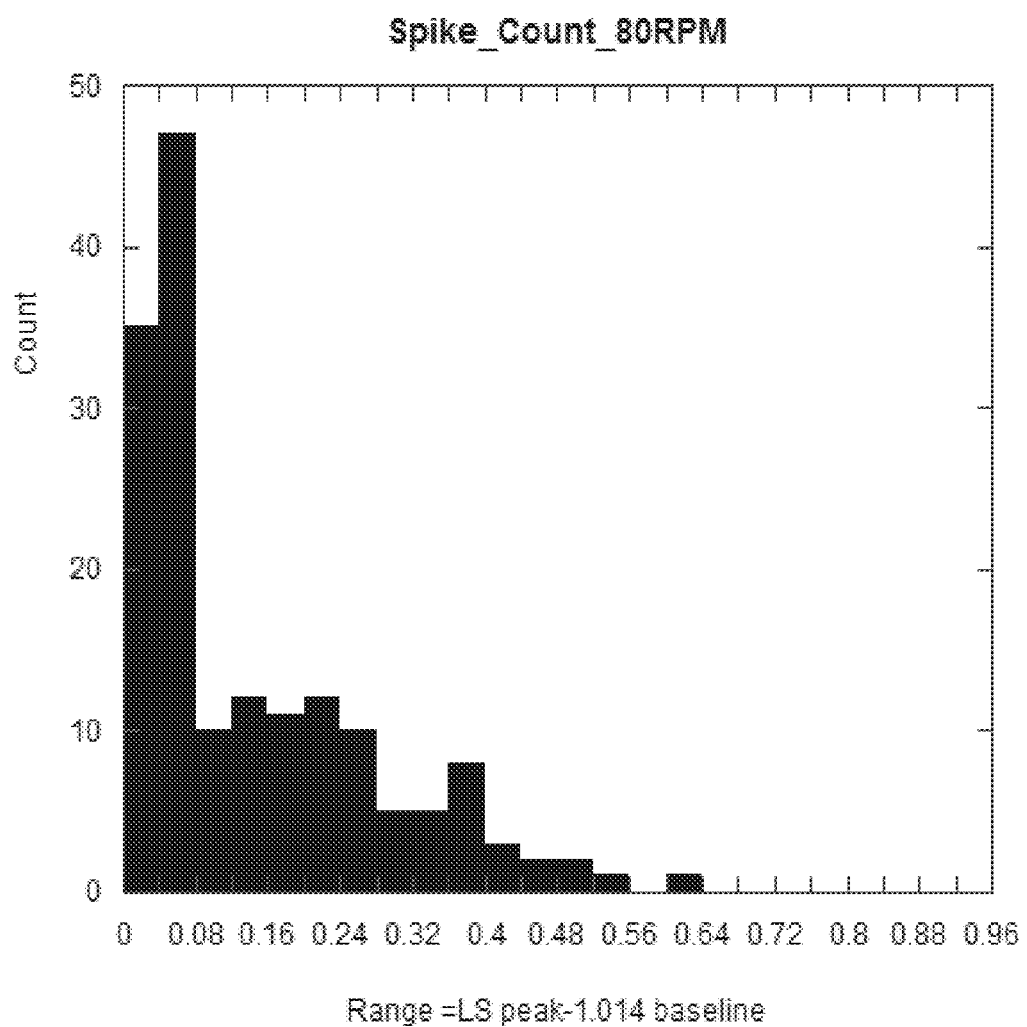
FIG. 14 illustrates an example histogram, taken from 2 micron spheres stirred at 80 RPM in an SMSLS square batch cell of side length 1 cm.

The probability distribution $W(I_R,M)$, can be determined experimentally from a single type of mass M of monodisperse particles, e.g. latex spheres. FIG. 14 is an example histogram, taken from 2 micron spheres stirred at 80 RPM in an SMSLS square batch cell of side length 1 cm. For characterizing any particular solution the LSS spectrum is measured in time, such as the examples shown above for large particles forming in protein solutions. These spectra show when large particles begin to form and, using the methods of Schimanowski et al., the number density of particles can be computed, and using the methods of the disclosed technology the MWD and/or its averages can be computed. More elaboration on inversion of the integral relating $S(I_R)$ to $N(M)$ is not provided here, but several approaches can be used, including analytical inversion with Fourier or other transforms, histogram, distribution-averaging, and other methods.

It is reminded that use of beam uniformization optics would greatly reduce the statistical tasks involved in implementing the analysis procedures, especially those for determination of MWD and its averages. With beam uniformization the histogram below would be a narrow spike. All particles passing through the uniform intensity in $V_s$ would yield the same scattering peak height, or at least nearly the same. The difference in the LSS in a uniform beam would be merely their width, accounting for different transit routes through, or 'dwell times' in $V_s$.

Example embodiments have been described hereinabove regarding improved systems and methods for the characterization of polymer and colloid solutions. Various modifications to and departures from the disclosed example embodiments will occur to those having ordinary skill in the art. The subject matter that is intended to be within the spirit of this disclosure is set forth in the following claims.

The invention claimed is:

1. A simultaneous multiple sample light scattering (SMSLS) detection device comprising:
   a plurality of light scattering batch cells, each of the light scattering batch cells configured to contain a solution;
   a plurality of stressor modules each respectively coupled to at least one of the plurality of light scattering batch cells and each respectively configured to introduce a stressor to the solutions contained in at least one of the plurality of light scattering batch cells, the plurality of stressor modules further configured to generate stressor information output data;
   a photodetector coupled to at least one of the plurality of light scattering batch cells configured to detect scattered light and generate light scattering data; and
   a computing device coupled to the plurality of stressor modules and the photodetector, the computing device configured to receive light scattering data from the photodetector and stressor information output data from the plurality of stressor modules, the computing device further configured to determine a time dependent response of a solution initiated by the introduction of a stressor from the light scattering data and the stressor information output data.

2. The SMSLS device of claim 1, wherein each of the plurality of light scattering batch cells comprises an agitation device capable of generating mechanical agitation of a solution contained therein, each agitation device coupled to at least one of the plurality of stressor modules, and wherein at least one of the plurality of stressor modules is configured to cause the agitation device to generate mechanical agitation of a solution.

3. The SMSLS device of claim 1, further comprising:
   an incident light source configured to supply incident light to the plurality of light scattering batch cells;
   a rastering device coupled to at least one of the plurality of light scattering batch cells that is configured to move the at least one light scattering batch cell in a controlled pattern through the incident light; and
   wherein the photodetector is further configured to detect the scattered light emitted through the rastered light scattering batch cell.

4. The SMSLS device of claim 1, wherein the plurality of stressor modules are configured to introduce a first stressor to at least one of the plurality of light scattering batch cells, and to introduce a second stressor to at least one other light scattering batch cell of the plurality of light scattering batch cells.

5. The SMSLS device of claim 4, wherein the second stressor is different than the first stressor, and wherein the plurality of stressor modules are configured to introduce the first stressor and second stressor simultaneously.

6. The SMSLS device of claim 1, wherein each of the plurality of stressor modules are configured to independently control the introduction of a stressor to a respective one of the light scattering batch cells.

7. The SMSLS device of claim 1, wherein the time dependent response is protein aggregation or protein degradation.

8. The SMSLS device of claim 1, wherein the light scattering data comprises light scattering spikes (LSS).

9. The SMSLS device of claim 1, wherein the solution comprises a protein and the plurality of stressor modules are configured to introduce a stressor to the solutions contained in the plurality of light scattering batch cells in order to initiate a protein aggregation or degradation response.

10. The SMSLS device of claim 1, wherein the light scattering data comprises a time dependent light scattering signature and the computing device is configured to determine a mechanistic or kinetic parameter associated with protein aggregation or protein degradation.

11. The SMSLS device of claim 1, further comprising one or more individual cell control modules respectively coupled to at least one of the plurality of light scattering batch cells and configured to introduce a solution to a respective one of the plurality of light scattering batch cells.

12. A method of determining a time dependent aggregation or degradation response of a biological solution to one or more stressors, the method comprising:
   introducing a biological solution to each of a plurality of light scattering cells;
   introducing, using a stressor module, one or more stressors to at least one biological solution contained in the plurality of light scattering cells;
   generating, at the stressor module, stressor information output data corresponding to the one or more stressors;
   introducing a source of incident light to the plurality of light scattering cells;
   detecting, at a photodetector, scattered light corresponding to a time dependent response in the at least one biological solution;
   generating, at the photodetector, light scattering data corresponding to the time dependent response;
   determining, at a computing device, a time dependent aggregation or degradation response of the at least one biological solution to the one or more stressors, using the light scattering data and the stressor information output data.

13. The method of claim 12, wherein the stressor is selected from the group consisting of mechanical agitation, ultrasound, a freeze-thaw cycle, increased exposure to an air/liquid interface, and exposure to a surface or a gas.

14. The method of claim 12, further comprising introducing, using a stressor module, a first stressor and a second stressor to the same biological solution.

15. The method of claim 14, wherein the first stressor is mechanical shear and the second stressor is increased exposure to an air/liquid interface.

16. The method of claim 12, further comprising introducing, using a stressor module, a first stressor to a first biological solution contained in the plurality of light scattering cells, and a second stressor to a second biological solution contained in the plurality of light scattering cells.

17. The method of claim 16, wherein the second stressor is different than the first stressor, and wherein the first and second stressors are introduced contemporaneously.

18. The method of claim 12, wherein introducing a biological solution comprises introducing a biological solution using an individual cell control module.

19. The method of claim 12, wherein the plurality of light scattering cells are batch cells.

20. The method of claim 12, wherein the biological solution is a protein solution.

21. A simultaneous multiple sample light scattering (SMSLS) detection device comprising:
- a plurality of light scattering batch cells, each of the light scattering batch cells configured to contain a solution;
- one or more individual cell control modules respectively coupled to at least one of the plurality of light scattering batch cells and configured to introduce a solution to a respective one of the plurality of light scattering batch cells;
- a plurality of stressor modules each respectively coupled to at least one of the plurality of light scattering batch cells and each respectively configured to introduce a stressor to the solutions contained in at least one of the plurality of light scattering batch cells, the plurality of stressor modules further configured to generate stressor information output data;
- a photodetector coupled to at least one of the plurality of light scattering batch cells configured to detect scattered light and generate light scattering data; and
- a computing device coupled to the plurality of stressor modules and the photodetector, the computing device configured to receive light scattering data from the photodetector and stressor information output data from the plurality of stressor modules, the computing device further configured to determine a time dependent response of a solution initiated by the introduction of a stressor from the light scattering data and the stressor information output data.

* * * * *